United States Patent
Golden et al.

(10) Patent No.: US 10,493,064 B2
(45) Date of Patent: Dec. 3, 2019

(54) IBS MICROBIOTA AND USES THEREOF

(71) Applicant: Salix Pharmaceuticals, Inc., Bridgewater, NJ (US)

(72) Inventors: Pam Golden, Durham, NC (US); Anthony Fodor, Charlotte, NC (US); Enoch Bortey, Chapel Hill, NC (US); William Forbes, Raleigh, NC (US)

(73) Assignee: Salix Pharmaceuticals, Inc., Bridgewater, NJ (US)

( * ) Notice: Subject to any disclaimer, the term of this patent is extended or adjusted under 35 U.S.C. 154(b) by 0 days.

(21) Appl. No.: 15/342,739

(22) Filed: Nov. 3, 2016

(65) Prior Publication Data

US 2017/0151220 A1 Jun. 1, 2017

Related U.S. Application Data

(63) Continuation of application No. PCT/US2015/029040, filed on May 4, 2015.

(60) Provisional application No. 62/135,658, filed on Mar. 19, 2015, provisional application No. 62/036,085, filed on Aug. 11, 2014, provisional application No. 61/988,841, filed on May 5, 2014, provisional application No. 61/988,293, filed on May 4, 2014.

(51) Int. Cl.
| | | |
|---|---|---|
| *A61K 31/437* | (2006.01) | |
| *C07G 11/00* | (2006.01) | |
| *C12Q 1/04* | (2006.01) | |
| *C12Q 1/6883* | (2018.01) | |
| *C12Q 1/689* | (2018.01) | |
| *C12Q 1/6809* | (2018.01) | |

(52) U.S. Cl.
CPC ............ *A61K 31/437* (2013.01); *C12Q 1/689* (2013.01); *C12Q 2600/158* (2013.01)

(58) Field of Classification Search
None
See application file for complete search history.

(56) References Cited

U.S. PATENT DOCUMENTS

| | | |
|---|---|---|
| 8,309,569 B2 | 11/2012 | Forbes et al. |
| 2007/0207231 A1 | 9/2007 | Thomas et al. |
| 2008/0193373 A1 | 8/2008 | Stritzker et al. |
| 2009/0305267 A1 | 12/2009 | Krause et al. |
| 2010/0239664 A1 | 9/2010 | Gushurst et al. |
| 2012/0165215 A1* | 6/2012 | Andersen ............ C12Q 1/6837 506/9 |
| 2012/0238468 A1* | 9/2012 | Tuk ..................... C12Q 1/04 506/9 |
| 2012/0264637 A1 | 10/2012 | Wiener-Kronish et al. |
| 2013/0184302 A1 | 7/2013 | Bortey et al. |
| 2013/0210852 A1 | 8/2013 | DuPont et al. |

FOREIGN PATENT DOCUMENTS

| | | |
|---|---|---|
| WO | 2011/043654 A1 | 4/2011 |
| WO | 2012080753 A1 | 6/2012 |

OTHER PUBLICATIONS

Moreau et al. (2014) Illumine sequencing of the V4 hypervariable region 16S rRNA gene reveals extensive changes in bacterial communities in the cecum following carbohydrate oral infusion and development of early-stage acute laminitis in the horse. Veterinary Microbiology, 168:436-441 (Year: 2014).*
Mizrahi-Man et al. (2013) Taxonomic Classification of Bacterial 16S rRNA Genes Using Short Sequencing Reads: Evaluation of Effective Study Designs. PLoS One, 8(1):e53608 (Year: 2013).*
Saulnier et al. (2011) Gastrointestinal Microbiome Signatures of Pediatric Patients With Irritable Bowel Syndrome. Gastroenterology, 141:1782-1791 (Year: 2011).*
Nelson et al. (2010) PhyloChip microarray analysis reveals altered gastrointestinal microbial communities in a rat model of colonic hypersensitivity. Neurogastroenterology & Motility, 23:169-e42 (Year: 2010).*
Kumar et al. (2011) Target Region Selection Is a Critical Determinant of Community Fingerprints Generated by 16S Pyrosequencing. PLoS One, 6(6):e20956, pp. 1-8 (Year: 2011).*
Menees et al. (2011) The Efficacy and Safety of Rifaximin for the Irritable Bowel Syndrome: A Systematic Review and Meta-Analysis. The American Journal of Gastroenterology, 107:28-35 (Year: 2011).*
Kim et al., "Evaluation of different partial 16S rRNA gene sequence regions for phylogenetic analysis of microbiomes," J. Microbiol Methods. 84(1): 81-7 (2010).
Kaakoush et al., "Microbial dysbiosis in pediatric patients with Crohn's disease," J Clin Microbial. 50(10): 3258-66 (2012).
Mukhopadhya et al. "A comprehensive evaluation of colonic mucosal isolates of Sutterella wadsworthensis from inflammatory bowel disease," PLoS One. 6(10): e27076, 1-10 (2011).
Bye, et al. Overgrowth of the indigenous gut microbiome and irritable bowel syndrome. World J Gastroenterol. 14;20(10):2449-55 (2014).
Frank et al. Molecular-phylogenetic characterization of microbial community imbalances in human inflammatory bowel diseases. Proc Natl Acad Sci U S A. 104(34):13780-5 (2007).
Jeffrey et al. An irritable bowel syndrome subtype defined by species-specific alterations in faecal microbiota. Gut. 61(7):997-1006 (2012).
Prantera et al. Rifaximin-extended intestinal release induces remission in patients with moderately active Crohn's disease. Gastroenterology. 142(3):473-481.e4 (2012).

(Continued)

*Primary Examiner* — Neil P Hammell
(74) *Attorney, Agent, or Firm* — McCarter & English, LLP; Jonathan M. Sparks; Michael J. DeGrazia

(57) ABSTRACT

The instant application provides methods of diagnosing and treating a subject having IBS. In certain embodiments, the methods also include diagnosing subjects who will respond to IBS treatment with rifaximin.

4 Claims, 16 Drawing Sheets

Specification includes a Sequence Listing.

(56) References Cited

OTHER PUBLICATIONS

Ye, Identification and Quantification of Abundant Species from Pyrosequences of 16S rRNA by Consensus Alignment. Proceedings of the IEEE Int Conf Bioinformatics Biomed. Feb. 4, 2011;2010;153-157.
Claesson et al., Comparative analysis of pyrosequencing and a phylogenetic microarray for exploring microbial community structures in the human distal intestine. PLoS One. Aug. 20, 2009;4(8):e6669. 15 pages.

* cited by examiner

IBS MICROBIOTA AND USES THEREOF

RELATED APPLICATIONS

This application is a continuation of International Application No. PCT/US2015/029040, filed on May 4, 2015, which claims the benefit of U.S. Provisional Application No. 61/988,293 filed May 4, 2014, U.S. Provisional Application No. 61/988,841 filed May 5, 2014, U.S. Provisional Application No. 62/036,085 filed Aug. 11, 2014, and U.S. Provisional Application No. 62/135,658 filed Mar. 19, 2015. The entire contents of the above-referenced applications are incorporated herein by reference.

SEQUENCE LISTING

The instant application contains a Sequence Listing which has been submitted electronically in ASCII format and is hereby incorporated by reference in its entirety. Said ASCII copy, created on Feb. 7, 2017, is named 119557-15005_SL.txt and is 881 bytes in size.

BACKGROUND

Irritable bowel syndrome (IBS) is a heterogeneous gastrointestinal (GI) disorder characterized by frequent and debilitating symptoms (e.g., diarrhea, bloating, abdominal pain, urgency to defecate, gas, and fecal incontinence), often with cyclical waxing and waning of symptoms. IBS causes substantial impairment in health-related quality of life (QOL), loss of work and productivity, social embarrassment, and high health care costs. The prevalence of IBS is believed to be 10 to 15% of the United States (US) population; however, only 15% of IBS patients actually seek medical treatment, which may be due in part to the lack of effective therapies. Despite the tremendous burden of IBS, on patients and the healthcare system, there remains a significant unmet need for effective and safe therapies, particularly for IBS with diarrhea (IBS-D).

The exact cause of IBS is unknown, but several hypotheses have been proposed. One prevalent hypothesis implicating enteric bacterial dysbiosis suggests that IBS symptoms are caused by alterations and abnormal colonization of the gut microbiome, which is also involved in normal physiological function. Enteric bacterial dysbiosis is best viewed as an altered microbial ecosystem and not an infection per se.

There is a need in the art to diagnosis those in need of treatment for IBS. There is also a need in the art to provide a prognostic indicator of those about to be treated or those that are being or have been treated for IBS.

There is also a need in the art for a method of providing symptomatic relief for subjects with IBS-D following a short treatment course along with a low risk of adversely contributing to concerns with multi-drug antibiotic resistance.

SUMMARY

Provided herein are methods of diagnosing and/or treating IBS.

In certain embodiments, methods also include diagnosing subjects who will respond to IBS treatment.

In certain embodiments, methods also include diagnosing subjects who will respond to rifaximin treatment for IBS.

In certain embodiments, methods also include diagnosing subjects who will respond to rifaximin treatment and retreatment for IBS.

In certain embodiments, treatment comprises 550 mg rifaximin TID for 14 days.

In certain embodiments, retreatment comprises 550 mg rifaximin TID for 14 days after a relapse from a first or other treatment.

The methods include determining the identity of the bacterial community (e.g., population) in the gastrointestinal (GI) tract.

The methods include determining the identity and prevalence of the bacterial community in the gastrointestinal (GI) tract.

In certain embodiments, the microbiome comprises the GI tract microbiome. In certain embodiments, the microbiome comprises the GI tract bacterial population. In certain embodiments, the microbiome comprises stool bacterial.

The methods include determining the identity of the bacteria in the gastrointestinal (GI) tract.

The methods include analysis of the microbiome by Meta genomics.

The methods include analysis of the identity of the bacterial community in the gastrointestinal (GI) microbiome to produce a profile of diversity of the bacterial communities.

The methods include determining the identity, prevalence and diversity of the gastrointestinal tract (GI) GI microbiome by Metagenomics.

The methods include analysis of the gastrointestinal (GI) microbiome by Metagenomics.

The methods include determining the identity of bacteria on one or more of the skin, nose, and GI tract.

The methods include determining the identity of bacteria on one or more of the skin, nose and GI tract by Metagenomics.

The methods include determining the identity and prevalence of bacteria on one or more of the skin, nose, and GI tract.

Provided herein are methods of treating a subject for IBS, comprising, determining and/or detecting and/or analyzing a subject's GI tract microbiome, using for example Metagenomics.

In certain embodiments, the method comprises treating a subject for IBS, comprising, determining and/or detecting and/or analyzing a subject's GI tract microbiome by Metagenomics.

In certain embodiments, the method comprises, administering rifaximin to a subject having particular bacteria, wherein the relative abundance of responder to a drug is higher than the relative abundance of non-responders is determined to be present.

In certain embodiments, the microbiome comprises the GI tract microbiome. In certain embodiments, the microbiome comprises the GI tract bacterial population. In certain embodiments, the microbiome comprises stool bacterial.

In certain embodiments, detecting comprises analyzing the 16S rRNA gene.

In certain embodiments, the V4 hyper-variable region of the 16S rRNA gene is analyzed.

In certain embodiments, the analysis of the taxa in Table 1, wherein the mean responder number is higher than the mean nonresponder number determined to be present, then the subject will respond to treatment.

In certain embodiments, the analysis of the taxa in Table 1, wherein the mean responder number is lower than the mean nonresponder number determined to be absent, then the subject will respond to treatment.

In certain embodiments, the analysis of the taxa in Table 1, wherein the mean nonresponder number is higher than the mean responder number determined to be present, then the subject will not respond to treatment.

In certain embodiments, the analysis of the taxa in Table 1 wherein the mean non responder number is lower than the mean responder number is determined to be absent, then the subject will not respond to treatment.

In certain embodiments, if a bacterial species, wherein the mean responder number is higher than the mean nonresponder number is determined to be present, then the subject will respond to treatment.

In certain embodiments, if a bacterial species wherein the mean responder number is lower than the mean nonresponder number is determined to be absent, then the subject will respond to treatment.

In certain embodiments, if a bacterial species wherein the mean nonresponder number is higher than the mean responder number is determined to be present, then the subject will not respond to treatment.

In certain embodiments, if a bacterial species, wherein the mean non responder number is lower than the mean responder number is determined to be absent, then the subject will not respond to treatment.

In certain embodiments, if Sutterellacae is present in an amount greater in a mean non-responder, then the subject will not respond to the treatment.

In certain embodiments, if Sutterellacae is present in an amount significantly greater in a mean non-responder then the subject will not respond to the treatment.

In certain embodiments, if Sphingobacteriaceae is present in an amount greater in a mean responder then the subject will respond to the treatment.

In certain embodiments, if Sphingobacteriaceae is present in an amount significantly greater in a mean responder then the subject will respond to the treatment.

In certain embodiments, if Phyllobacteriaceae is present in an amount greater in a mean responder then the subject will respond to the treatment.

In certain embodiments, if Phyllobacteriaceae is present in an amount significantly greater in a mean responder then the subject will respond to the treatment.

In certain embodiments, if Thermoanaerobacteraceae is present in an amount greater in a mean non-responder, then the subject will not respond to the treatment.

In certain embodiments, is present in an amount significantly greater in a mean non-responder, then the subject will not respond to the treatment.

In certain embodiments, if Burkholderiales incertae sedis is present in an amount greater in a mean non-responder, then the subject will not respond to the treatment.

In certain embodiments, if Burkholderiales incertae sedisis present in an amount significantly greater in a mean non-responder, then the subject will not respond to the treatment.

In certain embodiments, if Flavobacteriaceae is present in an amount greater in a mean responder then the subject will respond to the treatment.

In certain embodiments, if Flavobacteriaceae is present in an amount significantly greater in a mean responder then the subject will respond to the treatment.

In certain embodiments, if one or more of Sutterellacae, Thermoanaerobacteraceae or Burkholderiales incertae sedis are present in an amount greater in a mean non-responder, then the subject will not respond to the treatment.

In certain embodiments, if one or more of Sutterellacae, Thermoanaerobacteraceae or Burkholderiales incertae sedis are present in an amount significantly greater in a mean non-responder, then the subject will not respond to the treatment.

In certain embodiments, if one or more of Sphingobacteriaceae, Phyllobacteriaceae, or Flavobacteriaceae are present in an amount greater than a mean responder, then the subject will respond to the treatment.

In certain embodiments, if one or more of Sphingobacteriaceae, Phyllobacteriaceae, or Flavobacteriaceae are present in an amount significantly greater than a mean responder, then the subject will respond to the treatment.

In certain embodiments, if one or more of Sutterellacae, Thermoanaerobacteraceae or Burkholderiales incertae sedis are present in an amount greater in a mean non-responder, then the subject will not respond to the treatment and/or if one or more of Sphingobacteriaceae, Phyllobacteriaceae, or Flavobacteriaceae are present in an amount greater than a mean responder, then the subject will respond to the treatment.

In certain embodiments, if one or more of Sutterellacae, Thermoanaerobacteraceae or Burkholderiales incertae sedis are present in an amount significantly greater in a mean non-responder, then the subject will not respond to the treatment and/or if one or more of Sphingobacteriaceae, Phyllobacteriaceae, or Flavobacteriaceae are present in an amount significantly greater than a mean responder, then the subject will respond to the treatment.

Also provided herein are methods of providing a prognosis for treatment of IBS.

Provided herein are methods of selecting subjects for treatment with rifaximin.

Provided herein are methods of treating subjects having diarrhea-predominant IBS (d-IBS) with rifaximin comprising administering 550 mg of rifaximin three times daily (TID) to the subject for 14 days, followed by one or more subsequent treatments of rifaximin, wherein subsequent treatment is initiated upon the recurrence of signs or symptoms of IBS-related abdominal pain or 50% increase in the daily number of loose or watery stools within a week and wherein there is no effect on the subject's fecal microbiota population or the subject's cross-resistance to other antibiotics or the subject's predisposition to the emergence of microorganisms after the subsequent treatment of rifaximin.

In one embodiment, there is no effect on the subject's fecal microbiota general population.

In one embodiment, the effect on the subject's fecal microbiota is evaluated by Bray-Curtis similarity measures.

In one embodiment, the effect on the subject's fecal microbiota is evaluated by the Shannon Diversity Index.

In one embodiment, there is no effect on the subject's resistance to antibiotics other than rifampin.

In one embodiment, there is an effect on the subject's resistance to rifampin.

In one embodiment, there is no effect on the subject's cross-resistance to non-rifamycin antibiotics.

In one embodiment, the effect on the subject's cross-resistance to antibiotics is evaluated by the culture of isolates grown from a stool swab of the subject.

In one embodiment, the effect on the subject's cross-resistance to antibiotics is evaluated by the culture of isolates grown from a skin sample of the subject.

In one embodiment, the antibiotics comprise rifaximin, rifampin, vancomycin, fidaxomicin, metronidazole, ceftazidime, ceftriaxone, cephalothin, ciprofloxacin, imipenem, meropenem, pipercillin or tazobactam, trimethoprim, sulfamethoxazole or vancomycin.

In one embodiment, the antibiotics comprise rifaximin, rifampin, vancomycin, fidaxomicin, metronidazole, ceftazidime, ceftriaxone, ciprofloxacin, imipenem, meropenem, pipercillin or tazobactam.

In one embodiment, the antibiotics comprise rifaximin, rifampin, ceftazidime, ceftriaxone, cephalothin, ciprofloxacin, imipenem, meropenem, pipercillin or tazobactam, trimethoprim, sulfamethoxazole or vancomycin.

In one embodiment, there is no effect on the subject's predisposition to the emergence of microorganisms after the subsequent treatment of rifaximin.

In one embodiment, the subsequent treatments of rifaximin do not affect the subject's predisposition to the emergence of microorganisms in the subject's stool.

In one embodiment, the subsequent treatments of rifaximin do not affect the subject's predisposition to the emergence of microorganisms on the subject's skin.

In one embodiment, the microorganisms are yeast.

In one embodiment, the microorganisms are pathogenic bacteria.

In one embodiment, the microorganisms are gram positive bacteria.

In one embodiment, the microorganisms are gram negative bacteria.

In one embodiment, the pathogenic bacteria comprise species of *E. coli, Klebsiella, Pseudomonas, Enterobacter, Serratia, Proteus, Bacteroides, Enterococcus, Staphylococcus* or. *Clostridium difficile*.

In one embodiment, the pathogenic bacteria are *Staphylococcus* species.

In one embodiment, the pathogenic bacteria are *Enterococcus* species.

In one embodiment, the pathogenic bacteria are *Clostridium* specie.

In one embodiment, there is an effect on the subject's resistance to rifampin.

Provided herein are methods of treating subjects having diarrhea-predominant IBS (d-IBS) with rifaximin comprising: administering 550 mg of rifaximin three times daily (TID) to the subject for 14 days, followed by one or more subsequent treatments of rifaximin, wherein subsequent treatment is initiated upon the recurrence of signs or symptoms of IBS-related abdominal pain or 50% increase in the daily number of loose or watery stools within a week and wherein rifampin resistance tracks rifaximin resistance.

In one embodiment, an increase in rifampin resistance is observed in subjects who exhibit an increase in rifaximin resistance.

In one embodiment, no increase in rifampin resistance is observed in subjects who do not exhibit an increase in rifaximin resistance.

Provided herein are methods of treating subjects having diarrhea-predominant IBS (d-IBS) with rifaximin comprising: administering 550 mg of rifaximin three times daily (TID) to the subject for 14 days, followed by one or more subsequent treatments of rifaximin, wherein subsequent treatment is initiated upon the recurrence of signs or symptoms of IBS-related abdominal pain or 50% increase in the daily number of loose or watery stools within a week and wherein the subject exhibits transient changes in the rifaximin minimum inhibitory concentrations (MICs).

In one embodiment, the changes in MIC are reversible over time.

In one embodiment, the transient increase in MIC is exhibited against *Staphylococcus* species.

In one embodiment, the methods further comprise transient changes in the rifampin MICs.

In one embodiment, the changes in MIC are reversible over time.

Provided herein are methods of treating a subject having diarrhea-predominant IBS (d-IBS) with rifaximin comprising: administering 550 mg of rifaximin three times daily (TID) to the subject for 14 days, followed by one or more subsequent treatments of rifaximin, wherein subsequent treatment is initiated upon the recurrence of signs or symptoms of IBS-related abdominal pain or 50% increase in the daily number of loose or watery stools within a week and wherein changes in rifampin MICs is similar to changes in rifaximin MICs.

In one embodiment, similar to, comprises, for example, tracks, is in the same direction, changes by a similar amount or level.

Provided herein are methods of treating a subject having diarrhea-predominant IBS (d-IBS) with rifaximin comprising administering 550 mg of rifaximin three times daily (TID) to the subject for 14 days, followed by one or more subsequent treatments of rifaximin, wherein subsequent treatment is initiated upon the recurrence of signs or symptoms of IBS-related abdominal pain.

Provided herein are methods of treating a subject having diarrhea-predominant IBS (d-IBS) with rifaximin comprising administering 550 mg of rifaximin three times daily (TID) to the subject for 14 days, followed by one or more subsequent treatments of rifaximin, wherein subsequent treatment is initiated upon a 50% increase in the daily number of loose or watery stools within a week.

Provided herein are methods of treating a subject having diarrhea-predominant IBS (d-IBS) with rifaximin comprising administering 550 mg of rifaximin three times daily (TID) to the subject for 14 days, followed by one or more subsequent treatments of rifaximin, wherein there is no effect on the subject's fecal microbiota.

Provided herein are methods of treating a subject having diarrhea-predominant IBS (d-IBS) with rifaximin comprising administering 550 mg of rifaximin three times daily (TID) to the subject for 14 days, followed by one or more subsequent treatments of rifaximin, wherein there is no change to the subject's cross-resistance to antibiotics other than rifampin.

Provided herein are methods of treating a subject having diarrhea-predominant IBS (d-IBS) with rifaximin comprising administering 550 mg of rifaximin three times daily (TID) to the subject for 14 days, followed by one or more subsequent treatments of rifaximin, wherein there is no detectable change to the subject's predisposition to the emergence of microorganisms after the subsequent treatment of rifaximin.

Provided herein are methods of treating a subject having diarrhea-predominant IBS (d-IBS) with rifaximin comprising administering a first treatment, administering one or more subsequent treatments of rifaximin, wherein the one or more subsequent treatments leads to no evidence of significant effects on pathogen emergence in stool or skin samples of a subject, and wherein the treatment and each subsequent treatment with rifaximin comprises administering 550 mg of rifaximin three times daily (TID) to the subject for 14 days.

Provided herein are methods of treating a subject having diarrhea-predominant IBS (d-IBS) with rifaximin comprising administering a first treatment, administering one or more subsequent treatments of rifaximin, wherein the one or more subsequent treatments leads to no evidence of significant effects pathogen susceptibility in stool or skin samples of a subject, and wherein the treatment and each subsequent treatment with rifaximin comprises administering 550 mg of rifaximin three times daily (TID) to the subject for 14 days.

Provided herein are methods of treating a subject having diarrhea-predominant IBS (d-IBS) with rifaximin comprising administering a first treatment, administering one or more subsequent treatments of rifaximin, wherein the one or more subsequent treatments leads to no evidence of significant effects on the general microbial population in stool or skin samples of a subject, and wherein the treatment and each subsequent treatment with rifaximin comprises administering 550 mg of rifaximin three times daily (TID) to the subject for 14 days.

Provided herein are methods of diagnosing or treating irritable bowel syndrome (IBS) in a subject. The method includes analyzing a subject's sample for the presence or absence of one or more bacteria, said bacteria belonging to a taxon having a mean responder number higher than a mean nonresponder number, wherein the subject is responsive to rifaximin if said bacteria is detected and wherein the subject's sample comprises gastrointestinal microbiota from the subject; and administering rifaximin to the subject.

In some embodiments of the invention described herein, rifaximin is administered at a dosing regimen of 550 mg three times a day for 14 days.

In some embodiments of the invention described herein, the method further comprises repeating the dosing regimen upon recurrence of one or more symptoms associated with IBS.

In some embodiments of the invention described herein, said one or more symptoms include abdominal pain or loose or watery stools.

In some embodiments of the invention described herein, the method further comprises repeating the dosing regimen upon an increase of 50% or more in the daily number of loose or watery stools within a week.

In some embodiments of the invention described herein, the sample is a stool sample.

In some embodiments of the invention described herein, the presence of absence of the bacteria is determined by genomic analysis of bacterial DNA isolated from the sample, more specifically the 16S rRNA gene or the V4 hyper-variable region of the 16S rRNA gene.

In some embodiments of the invention described herein, the presence or absence of the bacteria is determined by amplifying the V4 hyper-variable region of the 16S rRNA gene and sequencing the amplified sequences of the V4 hyper-variable region.

In some embodiments of the invention described herein, the presence or absence of the bacteria is determined by bacterial culture, optionally in combination with genomic analysis.

In some embodiments of the invention described herein, said one or more bacteria belongs to one or more taxa selected from a group consisting of Sutterellaceae, Sphingobacteriaceae, Phyllobacteriaceae, Thermoanaerobactereraceae, Burkholderialees incertae sedis, and Flavobacteriaceae.

In some embodiments of the invention described herein, said one or more bacteria belongs to one or more taxa selected from a group consisting of Sutterellaceae, Thermoanaerobactereraceae, and Burkholderialees incertae sedis.

In some embodiments of the invention described herein, said one or more bacteria belongs to one or more taxa selected from a group consisting of Sphingobacteriaceae, Phyllobacteriaceae, and Flavobacteriaceae.

In some embodiments of the invention described herein, the mean responder number and mean non-responder number is determined based on a supervised classification of a gastrointestinal microbiota dataset for patients who were administered 550 mg of rifaximin TID for 14 days.

Provided herein are methods of treating irritable bowel syndrome (IBS), said method comprising administering rifaximin to a subject known to harbor one or more bacteria belonging to a taxon having a mean responder number higher than a mean nonresponder number, wherein rifaximin is administered to the subject at a dosing regimen of 550 mg three times a day for 14 days.

In some embodiments of the invention described herein, the method further comprises repeating the dosing regimen upon recurrence of one or more symptoms associated with IBS, for example, without exclusion, abdominal pain and/or loose or watery stools.

In some embodiments of the invention described herein, the method further comprises repeating the dosing regimen upon an increase of 50% or more in the daily number of loose or watery stools within a week.

In some embodiments of the invention described herein, said one or more bacteria belongs to one or more taxa selected from a group consisting of Sutterellaceae, Sphingobacteriaceae, Phyllobacteriaceae, Thermoanaerobactereraceae, Burkholderialees incertae sedis, and Flavobacteriaceae.

In some embodiments of the invention described herein, said one or more bacteria belongs to one or more taxa selected from a group consisting of Sutterellaceae, Thermoanaerobactereraceae, and Burkholderialees incertae sedis.

In some embodiments of the invention described herein, said one or more bacteria belongs to one or more taxa selected from a group consisting of Sphingobacteriaceae, Phyllobacteriaceae, and Flavobacteriaceae.

In some embodiments of the invention described herein, the mean responder number and mean non-responder number is determined based on a supervised classification of a gastrointestinal microbiota dataset for patients who were administered 550 mg of rifaximin TID for 14 days.

Also provided herein are methods of treating diarrhea-predominant IBS (d-IBS) in a subject, said method comprising administering rifaximin to the subject at a dosing regimen of 550 mg of rifaximin three times daily (TID) for 14 days; and repeating the dosing regimen upon an increase of 50% or more in the daily number of loose or watery stools within a week.

Also provided herein are methods of diagnosing rifaximin-responsive IBS in a subject by analyzing a subject's sample for the presence or absence of a bacteria, said bacteria having a mean responder number higher than a mean nonresponder number, wherein the subject is diagnosed with rifaximin-responsive IBS if said bacteria is detected and wherein the subject's sample contains gastrointestinal microbiota from the subject.

In some embodiments of the invention described herein, the IBS is d-IBS.

In some embodiments of the invention described herein, the sample is a stool sample.

In some embodiments of the invention described herein, the presence of absence of the bacteria is determined by genomic analysis of bacterial DNA isolated from the sample, for example, by analysis of the 16S rRNA gene, for example, by analysis of the V4 hyper-variable region of the 16S rRNA gene.

In some embodiments of the invention described herein, the presence or absence of the bacteria is determined by amplifying the V4 hyper-variable region of the 16S rRNA gene and sequencing the amplified sequences of the V4 hyper-variable region.

In some embodiments of the invention described herein, the presence or absence of the bacteria is determined by bacterial culture, optionally in combination with genomic analysis.

In some embodiments of the invention described herein, the mean responder number and mean non-responder number is determined based on a supervised classification of a gastrointestinal microbiota dataset for patients who were administered 550 mg of rifaximin TID for 14 days.

Other embodiments are disclosed infra.

DETAILED DESCRIPTION

Figure 1:
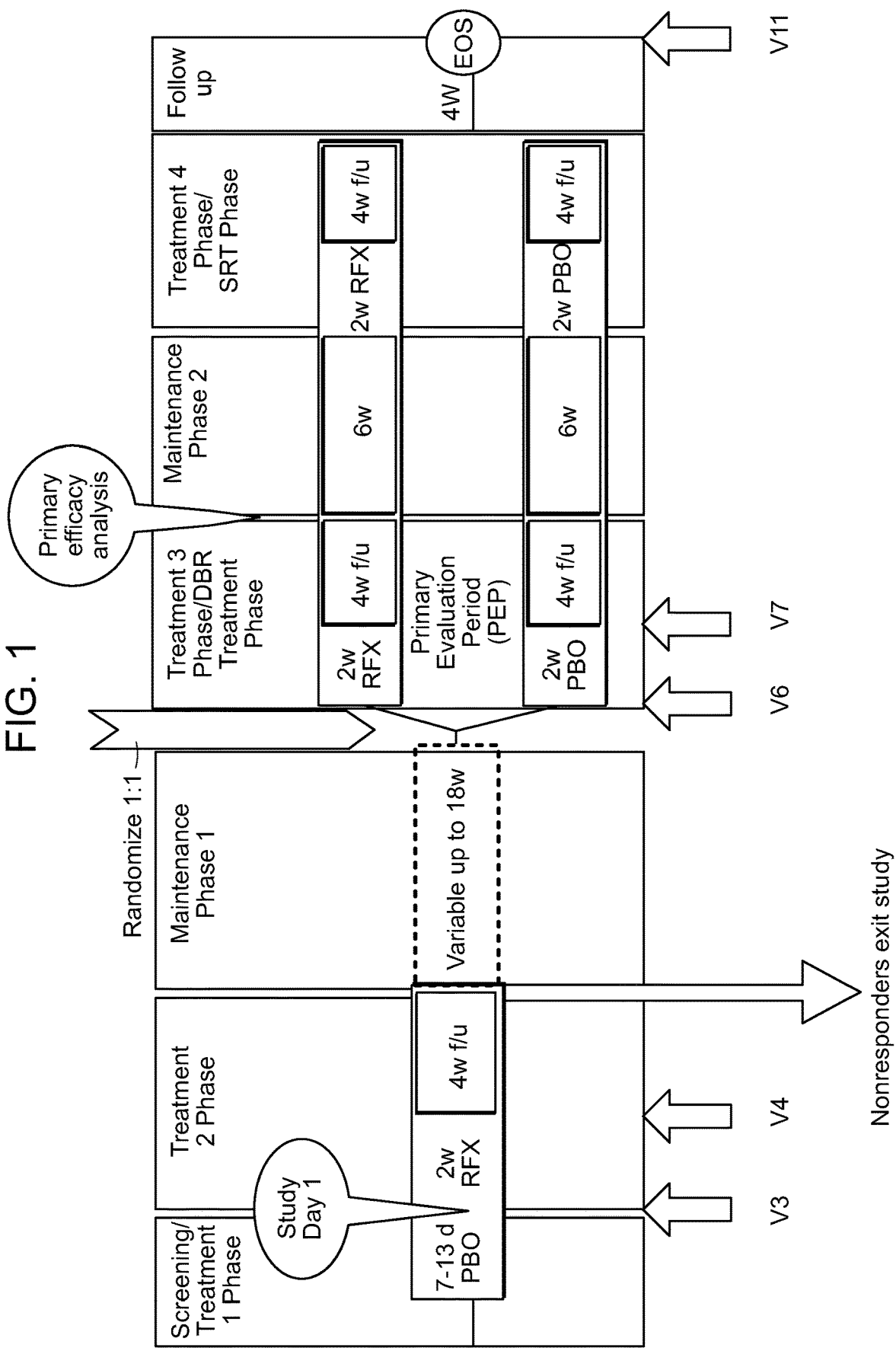
FIG. 1 shows the study design.

Multiple lines of evidence have implicated dysbiosis of the gut microbiome, and host response to that dysbiosis, as a cause of irritable bowel syndrome with diarrhea (IBS-D). The efficacy of rifaximin in the treatment of IBS-D has been established in a number of studies that showed statistically and clinically significant effects of the drug after single and multiple courses of treatment. The clinical pharmacology profile of rifaximin differentiates it from other antibiotics that have been tested for the treatment of IBS-D. Specifically, it is gut-targeted, resulting in minimal systemic exposure (orders of magnitude lower than systemic antibiotics or other minimally absorbed antibiotics), combined with high local concentrations in the GI tract after oral administration. Rifaximin activates the human pregnane X receptor, resulting in upregulation of host detoxification mechanisms and regulation of inflammatory processes that may modulate host response to dysbiosis. While rifaximin has demonstrable antimicrobial effects in vitro, data in the published literature indicate that it does not eradicate beneficial gut flora; data collected in this study provide verification of previously published findings in that regard. Additionally, rifaximin has been shown to alter bacterial virulence and attachment to host epithelia.

A common concern with antibiotic administration is the development of multi-drug antibiotic resistance by bacteria. The mechanism of bacterial resistance to rifamycins has been addressed in the literature; and one aspect of the invention presented herein shows that there is a low likelihood for the development of cross-resistance to non-rifamycin antibiotics, the poor fitness of rifamycin-resistant bacteria, and the lack of an apparent signal for development of clinically significant resistance.

The invention provided herein is based, in part, on the prospective evaluation of 16S rRNA bacterial deep gene sequencing data. From these data it is demonstrated that rifaximin treatment did not have significant effects on the Shannon diversity or evenness between placebo- and rifaximin-treated subjects with IBS-D, and had led to transient changes in the richness of the microbiota. These decreases in richness recovered following the end of the rifaximin treatment course.

It was also shown that of the bacterial families that were affected by rifaximin treatment, sequencing of the 16S rRNA gene revealed that low abundance taxa were more affected by rifaximin treatment than more abundant taxa. Overall, no disturbance of the stool microbiota was observed in subjects during repeat treatment with rifaximin as compared to subjects taking a single course of open-label rifaximin followed by double-blind placebo.

The invention herein is also based, in part, on a phase 3 study, which was designed to assess the efficacy of repeat treatment with rifaximin 550 TID for 2 weeks in IBS-D subjects who have previously responded to 2-week treatment with rifaximin 550 mg TID and are experiencing a recurrence of IBS symptoms.

The low systemic absorption of rifaximin, along with this microbiology data and the overall safety profile, supports the use of oral rifaximin as the most appropriate and well-characterized choice for the treatment of IBS-D and fulfills the need in the art for a method of providing symptomatic relief for subjects with IBS-D following a short treatment course along with a low risk of adversely contributing to concerns with multi-drug antibiotic resistance.

One clinical consideration regarding rifaximin resistance is the possibility of producing cross resistance to rifampin, a chemical analog of rifaximin Rifampin's value as an antibiotic in infectious diseases lies primarily in its treatment of tuberculosis. In the treatment of tuberculosis, rifampin is not used as a single agent, but is combined with other antitubercular antibiotics to lessen the likelihood of clinically significant resistance.

Rifaximin is a semi-synthetic antibiotic produced from rifamycin O. Rifaximin is a molecule belonging to the rifamycin class of antibiotics, e.g., a pyrido-imidazo rifamycin. Rifaximin exerts a broad antibacterial activity, for example, in the gastrointestinal tract against localized gastrointestinal bacteria that cause infectious diarrhea, irritable bowel syndrome, small intestinal bacterial overgrowth, Crohn's disease, and/or pancreatic insufficiency.

Rifaximin is also described in Italian Patent IT 1154655 and EP 0161534. EP patent 0161534 discloses a process for rifaximin production using rifamycin 0 as the starting material (The Merck Index, XIII Ed., 8301). U.S. Pat. No. 7,045,620 discloses polymorphic forms of rifaximin, as do U.S. Ser. No. 11/658,702; U.S. Ser. No. 61/031,329; U.S. Ser. No. 12/119,622; U.S. Ser. No. 12/119,630; U.S. Ser. No. 12/119,612; U.S. Ser. No. 12/119,600; U.S. Ser. No. 11/873,841; Publication WO 2006/094662; and U.S. Ser. No. 12/393,012. The applications and patents referred to here are incorporated herein by reference in their entirety for all purposes.

"Rifaximin", as used herein, includes solvates and polymorphous forms of the molecule, including, for example, Form α, Form β, Form γ Form δ, Form ε, Form ζ, Form η, Form τ, Form kappa, Form theta, From mu, From omicron, Form pi, Form lambda, Form xi, mesylate Form, amorphous Forms or solid dispersion form of rifaximin. These forms are described in more detail, for example, in EP 05 004 635.2, filed 3 Mar. 2005; U.S. Pat. Nos. 7,045,620; 7,612,199; 7,709,634; 7,915,275; 8,067,429; 8,193,196; 8,227,482; G. C. Viscomi, et al., Cryst Eng Comm, 2008, 10, 1074-1081 (April 2008), US Patent Publication No. 2010/0174064, US Patent Publication No. 2009/0028940, US Patent Publication No. 2005/0272754, US Patent Publication No. 2012/0077835 and U.S. Patent Publication No. 2012/0108620. Each of these references is hereby incorporated by reference in entirety.

The term "obtaining" as in "obtaining a GI specific antibiotic" is intended to include purchasing, synthesizing or otherwise acquiring a GI specific antibiotic. For example, obtaining rifaximin can include purchasing, synthesizing or otherwise acquiring rifaximin.

The term "pharmaceutical agent composition" (or agent or drug) as used herein refers to a chemical compound, composition, agent or drug capable of inducing a desired therapeutic effect when properly administered to a patient. It does not necessarily require more than one type of ingredient.

As used herein, "durability of response" includes, for example, adequate relief of symptoms after removal of treatment, continuous adequate relief of symptoms after removal of treatment, or response that is greater than or superior to placebo response. A response by a subject may be considered durable, for example, if they have a response to the rifamycin class antibiotic (e.g. rifaximin) after removal from treatment. The duration of response, may be, for example, 2 days, 7 days, two weeks, 3 weeks, 4 weeks, 12 weeks, between about 1 week and about 24 weeks or longer. In some embodiments, durability of response is a therapeutic effect that is observed for at least two months out of a three-month period. The response may be measured, for example using one or more of the methods outlined below, including, for example, a subject's subjective assessment of their symptoms or a healthcare provider's or caretaker's assessment of a subject's symptoms.

As used herein, "selecting subjects who respond," "selection of subjects who respond" or the like, include, for example, determining that a subject has responded to treatment based on a decrease of bowel disease (BD) or IBS symptoms and/or following label instructions to administer a product (e.g., a rifamycin class antibiotic) for a certain period of time or the like. The determination or selection may be based on the label (e.g., package or package insert) instructions or on the subject's subjective assessment of their symptoms or a healthcare provider's or caretaker's assessment of a subject's symptoms.

As used herein, a "responder" is a subject administered rifaximin for treatment of a disease, disorder or infection as described herein who responds to treatment by experiencing relief of symptoms, alleviation of discomfort or pain, or a general improvement in health relative to baseline. For example, a responder can be a subject administered rifaximin for treating IBS who has a positive response during at least 2 out of 4 weeks based on daily questions for the weekly responses for both abdominal pain and stool consistency. In one embodiment, a responder has a decrease in weekly average abdominal pain score and a reduction in the # of days per week with at least 1 stool with a consistency of greater than or equal to 6 (per the Bristol stool scale) as defined by the Rome III criteria.

In some embodiments, a responder can be identified as an IBS-D subject having one or more of the following: moderate bloating and abdominal pain, loose stools and/or bothersome urgency. For example, any one of the following criteria can be used to identify subject that are likely to respond to treatment with rifaximin: abdominal pain greater than or equal to, for example, 2, 2.5, 3, or 3.5; bloating greater than, for example, 2, 2.5, 3, or 3.5; loose stools with an average stool consistency score greater than or equal to 3, 3.5, 4, 4.5; or bothersome urgency for example greater than or equal to 3.0, 3.5, 4.0 or 4.5 days with urgency. Alternatively, two or more of the above-identified criteria can be used to identify subjects that are likely to respond to treatment with rifaximin. For example, abdominal pain and bloating; abdominal pain and loose stools, abdominal pain and bothersome urgency; abdominal pain, bloating and loose stools, etc.

A responder can also be defined as: 1) ≥30% improvement in abdominal pain, <4 in stool consistency, and ≥1 point decrease in daily IBS symptoms; 2) ≥30% improvement in abdominal pain, and ≥50% decrease in number of loose/watery stools within a given week comparing to the baseline; 3) ≥30% decrease in mean abdominal pain score from baseline using the worst 3 daily entries in a given week; 4) ≥30% decrease in the number of days with urgency within a given week comparing to the baseline; 5) ≥30% improvement in the selected worst baseline symptom; or 6) daily responder scores of 0 (not at all) or 1 (hardly) at least 50% of the days in a given week; OR 0 (not at all), 1 (hardly) or 2 (somewhat) 100% of days in a given week in the selected worst baseline symptom.

In a specific embodiment, a subject is defined as "a one month responder" if the subject has been administered rifaximin and is considered a responder at 2 weeks post treatment, wherein treatment comprises administering rifaximin for 14 days.

As used herein, a subject is considered to have a "recurrence" when criteria for a response is absent for at least 3 weeks during a 4 week period. Alternatively, "recurrence" can be defined as a worsening of one or more of stool consistency, abdominal pain or stool consistency and abdominal pain.

Provided herein are methods of treating, preventing, or alleviating disease, disorder or an infection comprising administering to a subject in need thereof an effective amount of rifaximin. The infection can be, for example, an infection caused by C. difficile. The disease or disorder can be, for example, a bowel-related disorder. Bowel related disorders (e.g., bowel diseases) include one or more of irritable bowel syndrome (IBS), alternating predominant IBS, diarrhea-predominant Irritable Bowel Syndrome (d-IBS, IBS-D), Crohn's disease, traveler's diarrhea, ulcerative colitis, enteritis, small intestinal bacterial overgrowth, chronic pancreatitis, pancreatic insufficiency, colitis, diverticular disease, hepatic encephalopathy, abdominal pain associated with IBS and/or pouchitis. In some embodiments, the bowel-related disorder is hepatic encephalopathy. In some embodiments, the bowel-related disorder is IBS. In one embodiment, IBS being treated by the methods described herein is mild, moderate or severe. In a specific embodiment, the IBS is severe. In another specific embodiment, the IBS is IBS-D.

*Clostridium difficile* is a Gram-positive anaerobic bacterium, and is deemed a significant human pathogen causing a spectrum of diseases ranging from mild diarrhea to fulminant pseudomembranous colitis (PMC). The bacterium is endemic in hospitals, and studies have shown that approximately one third of patients receiving antibiotic treatment in acute-care medical wards were colonized by *C. difficile* while in hospital (Kyne, L., et al., 2002, Clin. Infect. Dis. 34(3), pp 346-53, PMID: 11774082). Patients suffering from CDI respond well to treatment with vancomycin. However, the use of vancomycin is one of last resort since it is associated with several problems. Not only may it cause nephrotoxicity, ototoxicity, bone marrow toxicity and the red man syndrome, but vancomycin treatment often is not effective for treatment of CDI. Additionally, there is evidence that *C. difficile* is becoming at least partially resistant to vancomycin, demonstrating the need for new alternatives in the treatment of CDI.

Accordingly, provided herein are methods of treating, preventing, or alleviating *C. difficile* infection (CDI) in a subject, wherein the method includes administering to the subject an effective amount of rifaximin. In some embodiments, the subject is one who failed to respond to other therapies or treatment by antibiotics other than rifaximin. In some embodiments, the subject is one who failed to respond to treatment with vancomycin.

Also provided herein are methods of treating, preventing, or alleviating an antibiotic-resistant *C. difficile* infection, comprising administering rifaximin to a subject in need thereof, wherein administration of rifaximin is effective in treating the antibiotic-resistant CDI. In embodiments of the invention, a method of preventing CDI is provided, wherein the method comprises administering a non-systemic antibiotic to a subject in need of antibiotic treatment for a condition. In some embodiments, the condition is one selected from the group of: Crohn's disease, travelers' diarrhea, hepatic encephalopathy, minimal hepatic encephalopathy, irritable bowel syndrome, restless leg syndrome, dermal infections, small intestinal bacterial overgrowth, chronic pancreatitis, pancreatic insufficiency, diverticulitis, enteritis and colitis, skin infections, mucous membrane disorders, pouchitis, vaginal infections, anal fissures, ear infections, lung infections, periodontal conditions, rosacea, and other infections of the skin and/or other related conditions. In some embodiments, the non-systemic antibiotic is a rifaximin.

Rifaximin may be used in various treatment regimes. These regimes may vary depending upon the subject and the type of treatment. For example, rifaximin may be administered, for example, twice a day, three times a day, or four times or more often as necessary per day. Rifaximin may be administered in doses, for example of from about between 2 mg once daily to about 3000 mg TID. For example, rifaximin can be administered in daily doses of about 5 mg-100 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg, In some embodiments, rifaximin can be administered in daily doses of about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg. In some embodiments, rifaximin can be administered in daily doses of about 550 mg, about 600 mg, about 650 mg, about 700 mg, about 750 mg, about 800 mg, about 850 mg, about 900 mg, about 950 mg, or about 1000 mg. In some embodiments, rifaximin can be administered in daily doses of about 1100 mg about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, about 2500 mg, about 2600 mg, about 2700 mg, about 2800 mg, about 2900 mg, or about 3000 mg, In some embodiments, rifaximin can be administered in doses of about 25 mg BID, about 30 mg BID, about 35 mg BID, about 40 mg BID, about 45 mg BID, about 50 mg BID, about 55 mg BID, about 60 mg BID, about 65 mg BID, about 70 mg BID, about 75 mg BID, about 80 mg BID, about 85 mg BID, about 90 mg BID, about 95 mg BID, or about 100 mg BID. In some embodiments, rifaximin can be administered in doses of about 125 mg BID, about 150 mg BID, about 175 mg BID, about 200 mg BID, about 225 mg BID, about 250 mg BID, about 275 mg BID, about 300 mg BID, about 325 mg BID, about 350 mg BID, about 375 mg BID, about 400 mg BID, about 425 mg BID, about 450 mg BID, about 475 mg BID, or about 500 mg BID. In some embodiments, rifaximin can be administered in doses of about 550 mg BID, about 600 mg BID, about 650 mg BID, about 700 mg BID, about 750 mg BID, about 800 mg BID, about 850 mg BID, about 900 mg BID, about 950 mg BID, or about 1000 mg BID. In some embodiments, rifaximin can be administered in doses of about 1100 mg BID, about 1200 mg BID, about 1300 mg BID, about 1400 mg BID, about 1500 mg BID, about 1600 mg BID, about 1700 mg BID, about 1800 mg BID, about 1900 mg BID, about 2000 mg BID, about 2100 mg BID, about 2200 mg BID, about 2300 mg BID, about 2400 mg BID, about 2500 mg BID, about 2600 mg BID, about 2700 mg BID, about 2800 mg BID, about 2900 mg BID or about 3000 mg BID, In some embodiments, rifaximin can be administered in doses of about 25 mg TID, about 30 mg TID, about 35 mg TID, about 40 mg TID, about 45 mg TID, about 50 mg TID, about 55 mg TID, about 60 mg TID, about 65 mg TID, about 70 mg TID, about 75 mg TID, about 80 mg TID, about 85 mg TID, about 90 mg TID, about 95 mg TID, or about 100 mg TID. In some embodiments, rifaximin can be administered in doses of about 125 mg TID, about 150 mg TID, about 175 mg TID, about 200 mg TID, about 225 mg TID, about 250 mg TID, about 275 mg TID, about 300 mg TID, about 325 mg TID, about 350 mg TID, about 375 mg TID, about 400 mg TID, about 425 mg TID, about 450 mg TID, about 475 mg TID, or about 500 mg TID, In some embodiments, rifaximin can be administered in doses of about 550 mg TID, about 600 mg TID, about 650 mg TID, about 700 mg TID, about 750 mg TID, about 800 mg TID, about 850 mg TID, about 900 mg TID, about 950 mg TID, or about 1000 mg TID. In some embodiments, rifaximin can be administered in doses of about 1100 mg TID, about 1200 mg TID, about 1300 mg TID, about 1400 mg TID, about 1500 mg TID, about 1600 mg TID, about 1700 mg TID, about 1800 mg TID, about 1900 mg TID, about 2000 mg TID, about 2100 mg TID, about 2200 mg TID, about 2300 mg TID, about 2400 mg TID, about 2500 mg TID, about 2600 mg TID, about 2700 mg TID, about 2800 mg TID, about 2900 mg TID or about 3000 mg TID. The rifaximin may be administered, for example, in tablet form, powdered form, liquid form or in capsules. In some embodiments, rifaximin can be administered in a time-released formulation.

In some embodiments, rifaximin is administered as a soluble solid dispersion. For example, rifaximin can be administered at between about 2-550 mg of soluble solid dispersion of rifaximin.

In some embodiments, the rifaximin is administered to a subject from between about 1 week to about 6 weeks in duration, from between about 8 weeks to about 12 weeks in duration, or from between about 1 day to about 21 days in duration. In one embodiment, rifaximin is administered for 10 days. The rifaximin may be administered from between about 1 day and about 1 year, or from 1 week to about 52 weeks. The rifaximin may be administered intermittently or continuously during the course of treatment. Length of treatment may vary depending on the type and length of disease and the proper length of treatment may be easily determined by one of skill in the art having the benefit of this disclosure.

For any of the embodiments, rifaximin may be administered, for example, once daily, twice daily, three times daily, or four times daily (or more often as necessary for a particular subject) to a subject. In some embodiments, the methods comprise administering the rifaximin once daily to the subject because it may, for example, minimize the side effects and increase patient compliance. In some embodiments, rifaximin is administered twice and/or three times daily.

Dosages, according to certain preferred embodiments, range from between about 50 to about 6000 mg of rifaximin administered daily. For example, a dose of 400 mg may be administered to a subject three times daily, or a dose of 550 mg may be administered to a subject twice daily, or a 550 mg dose may be administered three times daily. Other appropriate dosages for the methods as disclosed herein may be determined by health care professionals or by the subject. The amount of rifaximin administered daily may be increased or decreased based on the weight, age, health, sex or medical condition of the subject. One of skill in the art would be able to determine the proper dose for a subject based on this disclosure.

While it was noted previously (Bajaj J S et al. Am J Physiol Gastrointest Liver Physiol. 2012; 302(1):G168-G175) that there were correlations with microbiome, poor cognition, and markers of inflammation in patients with cirrhosis and HE as well as correlation between impairment on most cognition tests and relative abundance of Alcaligeneceae and Porphyromonadaceae taxa in patients with cirrhosis, and also that (Bajaj J S et al. Am J Physiol Gastrointest Liver Physiol. 2012; 303(6):G675-G685) there is an impact of rifaximin maintenance therapy on mucosal gut microbiota in patients with a history of HE (that there was a decreased abundance of autochthonous bacteria and Veillonellaceae, but an increased abundance of *Propionibacterium* in the rifaximin group), herein it has surprisingly been found that there exist specific bacteria, which either their presence or absence from a subject pretreatment can predict response and non-response to rifaximin treatment in IBS.

Provided herein are methods of diagnosing IBS.

In certain embodiments, methods also include diagnosing subjects who will respond to IBS treatment.

In certain embodiments, methods also include diagnosing subjects who will respond to rifaximin treatment for IBS.

In certain embodiments, methods also include diagnosing subjects who will respond to rifaximin treatment and retreatment for IBS.

In certain embodiments, treatment comprises 550 mg rifaximin TID for 14 days.

In certain embodiments, retreatment comprises 550 mg rifaximin TID for 14 days after a relapse from a first or other treatment.

The methods include determining the identity of the bacterial community (e.g., population) in the gastrointestinal (GI) tract.

The methods include determining the identity and prevalence of the bacterial community in the gastrointestinal (GI) tract.

In certain embodiments, the microbiome is the GI tract microbiome. In certain embodiments, the microbiome is the GI tract microbiome. In certain embodiments, the microbiome is the GI tract microbiome as represented by stool bacterial population.

The methods include determining the identity of the bacteria in the gastrointestinal (GI) tract.

The methods include analysis of the microbiome by Metagenomics.

The methods include analysis of the identity of the bacterial community in the gastrointestinal (GI) microbiome to produce a profile of diversity of the bacterial communities.

The methods include determining the identity, prevalence and diversity of the gastrointestinal tract (GI) GI microbiome by Metagenomics.

The methods include analysis of the gastrointestinal (GI) microbiome by Metagenomics.

The methods include determining the identity of bacteria on one or more of the skin, nose, and GI tract.

The methods include determining the identity of bacteria on one or more of the skin, nose and GI tract by Metagenomics.

The methods include determining the identity and prevalence of bacteria on one or more of the skin, nose, and GI tract.

Provided herein are methods of treating a subject for IBS, comprising, determining and/or detecting and/or analyzing a subject's GI tract microbiome, using for example Metagenomics.

In certain embodiments, the method comprises treating a subject for IBS, comprising, determining and/or detecting and/or analyzing a subject's GI tract microbiome by Metagenomics.

In certain embodiments, the method comprises, administering rifaximin to a subject having particular bacteria, for which the relative abundance of responder to a drug is determined to be higher than the relative abundance of non-responders.

In certain embodiments, the microbiome is the GI tract microbiome. In certain embodiments, the microbiome is the GI tract bacterial population. In certain embodiments, the microbiome is the GI tract bacterial population as represented by stool bacterial population.

In certain embodiments, detecting comprises analyzing the 16S rRNA gene.

In certain embodiments, the V4 hyper-variable region of the 16S rRNA gene is analyzed.

In certain embodiments, the analysis and detection of the taxa in Table 1, for which the mean responder number is higher than the mean nonresponder number indicates the subject will respond to treatment.

In certain embodiments, the analysis and determined absence of the taxa in Table 1, for which the mean responder number is lower than the mean nonresponder number indicates the subject will respond to treatment.

In certain embodiments, the analysis and detection of the taxa in Table 1, for which the mean nonresponder number is higher than the mean responder number indicates the subject will not respond to treatment.

In certain embodiments, the analysis and determined absence of the taxa in Table 1 wherein the mean non responder number is lower than the mean responder number then the subject will not respond to treatment.

In certain embodiments, if a bacterial species, for the mean responder number is higher than the mean nonresponder number, is determined to be present, then the subject will respond to treatment.

In certain embodiments, if a bacterial species for which the mean responder number is lower than the mean nonresponder number is determined to be absent, then the subject will respond to treatment.

In certain embodiments, if a bacterial species for which the mean nonresponder number is higher than the mean responder number is determined to be present, then the subject will not respond to treatment.

In certain embodiments, if a bacterial species for which the mean non responder number is lower than the mean responder number is determined to be absent, then the subject will not respond to treatment.

In certain embodiments, if Sutterellacae is present in an amount greater in a mean non-responder, then the subject will not respond to the treatment.

In certain embodiments, if Sutterellacae is present in an amount significantly greater in a mean non-responder then the subject will not respond to the treatment.

In certain embodiments, if Sphingobacteriaceae is present in an amount greater in a mean responder then the subject will respond to the treatment.

In certain embodiments, if Sphingobacteriaceae is present in an amount significantly greater in a mean responder then the subject will respond to the treatment.

In certain embodiments, if Phyllobacteriaceae is present in an amount greater in a mean responder then the subject will respond to the treatment.

In certain embodiments, if Phyllobacteriaceae is present in an amount significantly greater in a mean responder then the subject will respond to the treatment.

In certain embodiments, if Thermoanaerobacteraceae is present in an amount greater in a mean non-responder, then the subject will not respond to the treatment.

In certain embodiments, if Thermoanaerobacteraceae is present in an amount significantly greater in a mean non-responder, then the subject will not respond to the treatment.

In certain embodiments, if Burkholderiales incertae sedis is present in an amount greater in a mean non-responder, then the subject will not respond to the treatment.

In certain embodiments, if Burkholderiales incertae sedisis present in an amount significantly greater in a mean non-responder, then the subject will not respond to the treatment.

In certain embodiments, if Flavobacteriaceae is present in an amount greater in a mean responder then the subject will respond to the treatment.

In certain embodiments, if Flavobacteriaceae is present in an amount significantly greater in a mean responder then the subject will respond to the treatment.

In certain embodiments, if one or more of Sutterellacae, Thermoanaerobacteraceae or Burkholderiales incertae sedis are present in an amount greater in a mean non-responder, then the subject will not respond to the treatment.

In certain embodiments, if one or more of Sutterellacae, Thermoanaerobacteraceae or Burkholderiales incertae sedis are present in an amount significantly greater in a mean non-responder, then the subject will not respond to the treatment.

In certain embodiments, if one or more of Sphingobacteriaceae, Phyllobacteriaceae, or Flavobacteriaceae are present in an amount greater than a mean responder, then the subject will respond to the treatment.

In certain embodiments, if one or more of Sphingobacteriaceae, Phyllobacteriaceae, or Flavobacteriaceae are present in an amount significantly greater than a mean responder, then the subject will respond to the treatment.

In certain embodiments, if one or more of Sutterellacae, Thermoanaerobacteraceae or Burkholderiales incertae sedis are present in an amount greater in a mean non-responder, then the subject will not respond to the treatment and/or if one or more of Sphingobacteriaceae, Phyllobacteriaceae, or Flavobacteriaceae are present in an amount greater than a mean responder, then the subject will respond to the treatment.

In certain embodiments, if one or more of Sutterellacae, Thermoanaerobacteraceae or Burkholderiales incertae sedis are present in an amount significantly greater in a mean non-responder, then the subject will not respond to the treatment and/or if one or more of Sphingobacteriaceae, Phyllobacteriaceae, or Flavobacteriaceae are present in an amount significantly greater than a mean responder, then the subject will respond to the treatment.

In certain embodiments, if Sutterellacae is present, then the subject will not respond to the treatment.

In certain embodiments, if Sphingobacteriaceae is present, then the subject will respond to the treatment.

In certain embodiments, if Phyllobacteriaceae is present, then the subject will respond to the treatment.

In certain embodiments, if Thermoanaerobacteraceae is present, then the subject will not respond to the treatment.

In certain embodiments, if Burkholderiales incertae sedis is present, then the subject will not respond to the treatment.

In certain embodiments, if Flavobacteriaceae is present, then the subject will respond to the treatment.

In certain embodiments, if one or more of Sutterellacae, Thermoanaerobacteraceae or Burkholderiales incertae sedis are present, then the subject will not respond to the treatment.

In certain embodiments, if one or more of Sphingobacteriaceae, Phyllobacteriaceae, or Flavobacteriaceae are present, then the subject will respond to the treatment.

In certain embodiments, if one or more of Sutterellacae, Thermoanaerobacteraceae or Burkholderiales incertae sedis are present, then the subject will not respond to the treatment and/or if one or more of Sphingobacteriaceae, Phyllobacteriaceae, or Flavobacteriaceae are present, then the subject will respond to the treatment.

Also provided herein are methods of providing a prognosis for treatment of IBS.

Provided herein are methods of selecting subjects for treatment with rifaximin. Provided herein are methods of diagnosing or treating irritable bowel syndrome (IBS) in a subject. The method includes analyzing a subject's sample for the presence or absence of one or more bacteria, said bacteria belonging to a taxon having a mean responder number higher than a mean nonresponder number, wherein the subject would be responsive to rifaximin if said bacteria is detected and wherein the subject's sample comprises gastrointestinal microbiota from the subject; and administering rifaximin to the subject.

In some embodiments of the invention described herein, rifaximin is administered at a dosing regimen of 550 mg three times a day for 14 days.

In some embodiments of the invention described herein, the method further comprises repeating the dosing regimen upon recurrence of one or more symptoms associated with IBS.

In some embodiments of the invention described herein, said one or more symptoms include abdominal pain or loose or watery stools.

In some embodiments of the invention described herein, the method further comprises repeating the dosing regimen upon an increase of 50% or more in the daily number of loose or watery stools within a week.

In some embodiments of the invention described herein, the sample is a stool sample.

In some embodiments of the invention described herein, the presence of absence of the bacteria is determined by genomic analysis of bacterial DNA isolated from the sample, more specifically the 16S rRNA gene or the V4 hyper-variable region of the 16S rRNA gene.

In some embodiments of the invention described herein, the presence or absence of the bacteria is determined by amplifying the V4 hyper-variable region of the 16S rRNA gene and sequencing the amplified sequences of the V4 hyper-variable region.

In some embodiments of the invention described herein, the presence or absence of the bacteria is determined by bacterial culture, optionally in combination with genomic analysis.

In some embodiments of the invention described herein, said one or more bacteria belongs to one or more taxa selected from a group consisting of Sutterellaceae, Sphingobacteriaceae, Phyllobacteriaceae, Thermoanaerobacteraceae, Burkholderialees incertae sedis, and Flavobacteriaceae.

In some embodiments of the invention described herein, said one or more bacteria belongs to one or more taxa selected from a group consisting of Sutterellaceae, Thermoanaerobactereraceae, and Burkholderialees incertae sedis.

In some embodiments of the invention described herein, said one or more bacteria belongs to one or more taxa selected from a group consisting of Sphingobacteriaceae, Phyllobacteriaceae, and Flavobacteriaceae.

In some embodiments of the invention described herein, the mean responder number and mean non-responder number is determined based on a supervised classification of a gastrointestinal microbiota dataset for patients who were administered 550 mg of rifaximin TID for 14 days.

Provided herein are methods of treating irritable bowel syndrome (IBS), said method comprising administering rifaximin to a subject known to harbor one or more bacteria belonging to a taxon having a mean responder number higher than a mean nonresponder number, wherein rifaximin is administered to the subject at a dosing regimen of 550 mg three times a day for 14 days.

In some embodiments of the invention described herein, the method further comprises repeating the dosing regimen upon recurrence of one or more symptoms associated with IBS, for example, without exclusion, abdominal pain and/or loose or watery stools.

In some embodiments of the invention described herein, the method further comprises repeating the dosing regimen upon an increase of 50% or more in the daily number of loose or watery stools within a week.

In some embodiments of the invention described herein, said one or more bacteria belongs to one or more taxa selected from a group consisting of Sutterellaceae, Sphingobacteriaceae, Phyllobacteriaceae, Thermoanaerobactereraceae, Burkholderialees incertae sedis, and Flavobacteriaceae.

In some embodiments of the invention described herein, said one or more bacteria belongs to one or more taxa selected from a group consisting of Sutterellaceae, Thermoanaerobactereraceae, and Burkholderialees incertae sedis.

In some embodiments of the invention described herein, said one or more bacteria belongs to one or more taxa selected from a group consisting of Sphingobacteriaceae, Phyllobacteriaceae, and Flavobacteriaceae.

In some embodiments of the invention described herein, the mean responder number and mean non-responder number is determined based on a supervised classification of a gastrointestinal microbiota dataset for patients who were administered 550 mg of rifaximin TID for 14 days.

Also provided herein are methods of treating diarrhea-predominant IBS (d-IBS) in a subject, said method comprising administering rifaximin to the subject at a dosing regimen of 550 mg of rifaximin three times daily (TID) for 14 days; and repeating the dosing regimen upon an increase of 50% or more in the daily number of loose or watery stools within a week.

Also provided herein are methods of diagnosing rifaximin-responsive IBS in a subject by analyzing a subject's sample for the presence or absence of a bacteria, said bacteria having a mean responder number higher than a mean nonresponder number, wherein the subject is diagnosed with rifaximin-responsive IBS if said bacteria is detected and wherein the subject's sample contains gastrointestinal microbiota from the subject.

In some embodiments of the invention described herein, the IBS is d-IBS.

In some embodiments of the invention described herein, the sample is a stool sample.

In some embodiments of the invention described herein, the presence of absence of the bacteria is determined by genomic analysis of bacterial DNA isolated from the sample, for example, by analysis of the 16S rRNA gene, for example, by analysis of the V4 hyper-variable region of the 16S rRNA gene.

In some embodiments of the invention described herein, the presence or absence of the bacteria is determined by amplifying the V4 hyper-variable region of the 16S rRNA gene and sequencing the amplified sequences of the V4 hyper-variable region.

In some embodiments of the invention described herein, the presence or absence of the bacteria is determined by bacterial culture, optionally in combination with genomic analysis.

In some embodiments of the invention described herein, the mean responder number and mean non-responder number is determined based on a supervised classification of a gastrointestinal microbiota dataset for patients who were administered 550 mg of rifaximin TID for 14 days.

EXAMPLES

It will be appreciated that the invention should not be construed to be limited to the examples, which are now described; rather, the invention is construed to include any and all applications provided herein and all equivalent variations within the skill of the ordinary artisan.

Example 1

A study, examining stool samples across all collection times, characterized intestinal microbiota in terms of composition and diversity. (FIG. 1 shows the study design and defines the V3, V4, V6 time points). During the study, subjects provided stool samples at baseline and after two weeks of open-label rifaximin 550 mg TID respectively; stool samples were provided prior to and immediately after two weeks of double-blind retreatment with rifaximin 550 mg TID or placebo, and stool samples were provided at the end of study. Stool samples are separated into 2-mL aliquots in polypropylene cryovials, stored at ≤−20° C. at the clinical site, shipped on dry ice and stored long term at ≤−70° C.

Bacterial DNA were isolated from fecal samples, and the V4 hyper-variable region of the 16S rRNA gene is amplified using two-step PCR with Illumina HiSeq2000 sequencing technology.

The sequencing reactions were designed so that the forward and backward paired Illumina reads do not overlap. Forward and backward reads were treated as technical replicates with independent analyses.

Sequences were analyzed by two methods.

OTUs (operational taxonomic units) which are clusters of sequences that have on average 97% identity.
Number of Samples Sequenced:

| | |
|---|---|
| Treatment 2 (V3) | 101 |
| End of Treatment 2 (V4) | 102 |
| Treatment 3 (V6) | 69 |
| End of Treatment 3 (V7) | 72 |
| Follow up/End of Study | 96 |

Total of 449 samples * 2 paired end

Number of Sequences Called to Each Taxonomic Level at 50% Confidence by the RDP Pipeline

| | Total sequences | Average per sample | minimum number |
|---|---|---|---|
| phylum | 3,952,518,867 | 4,401,468 | 20,848 |
| class | 3,867,083,473 | 4,306,329 | 19,144 |
| order | 3,851,723,408 | 4,289,224 | 18,921 |
| family | 3,707,664,545 | 4,128,802 | 17,896 |
| genus | 3,150,141,444 | 3,507,952 | 14,623 |

Figure 2:
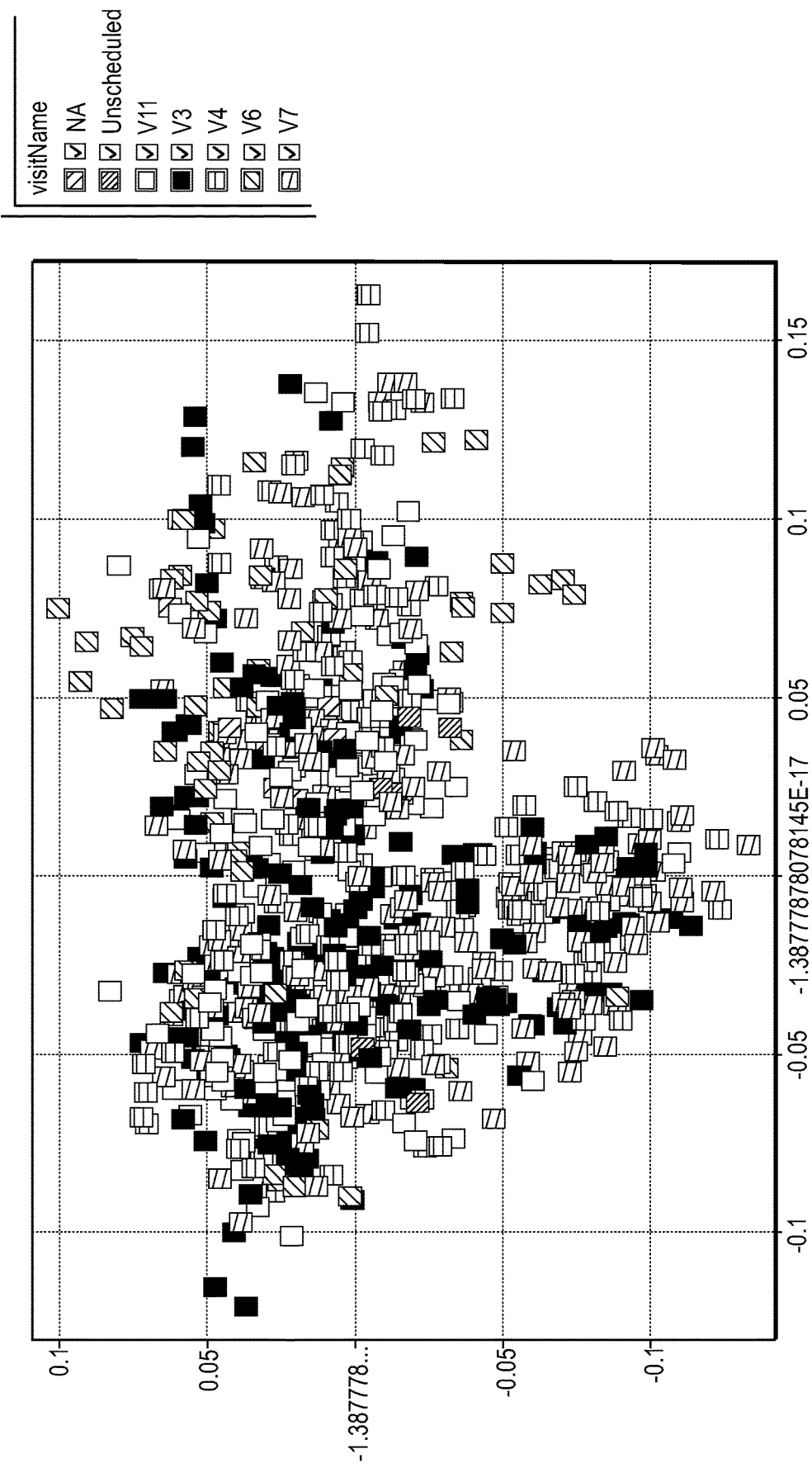
FIG. 2 shows an ordination plot with 449 samples*2 paired-end. There is no obvious clustering by visit date.

FIG. 2 shows an ordination plot with 449 samples 2 paired-end. There is no obvious clustering by visit date.

Figure 3:
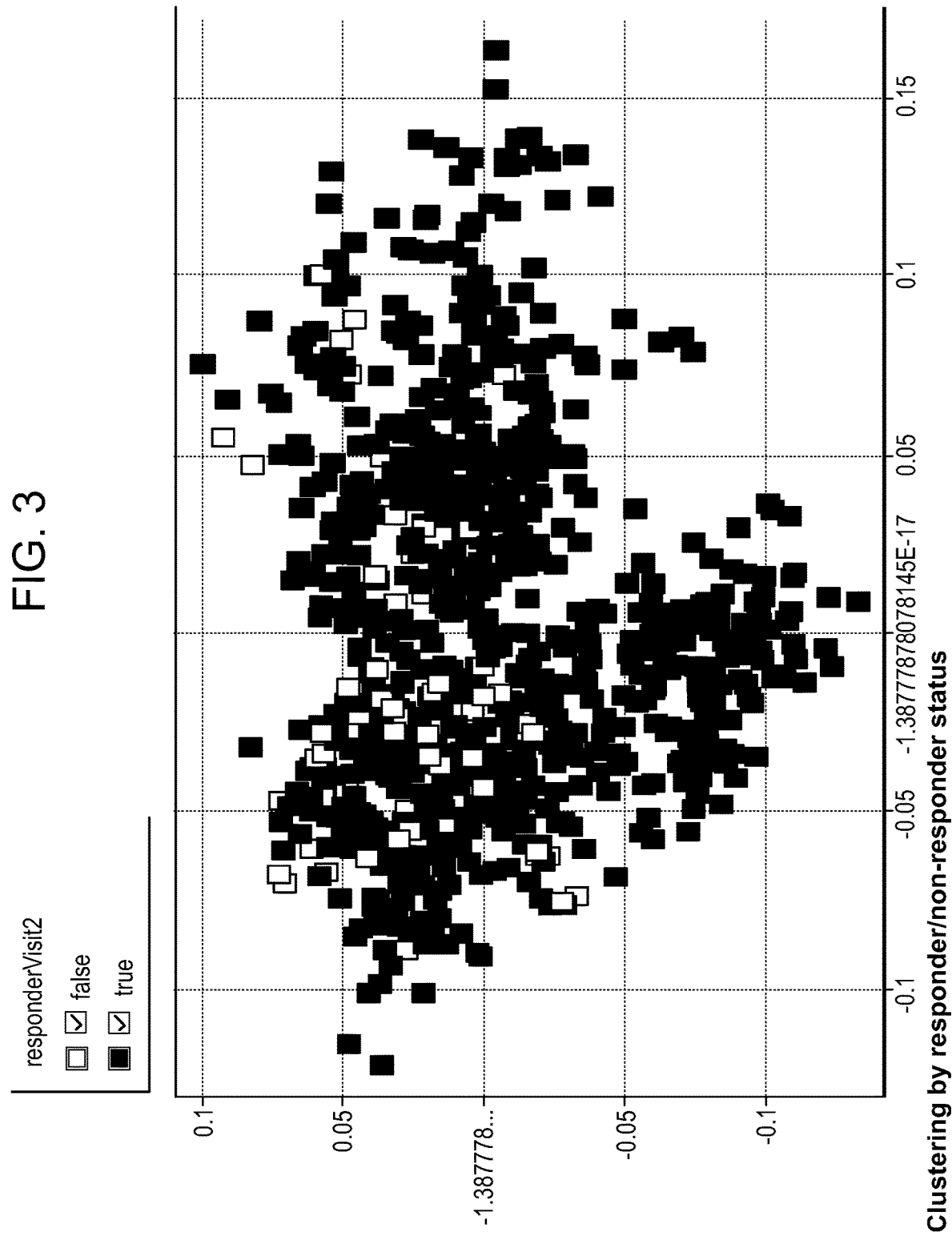
FIG. 3 shows clustering by responder/non-responder status.
Figure 4:
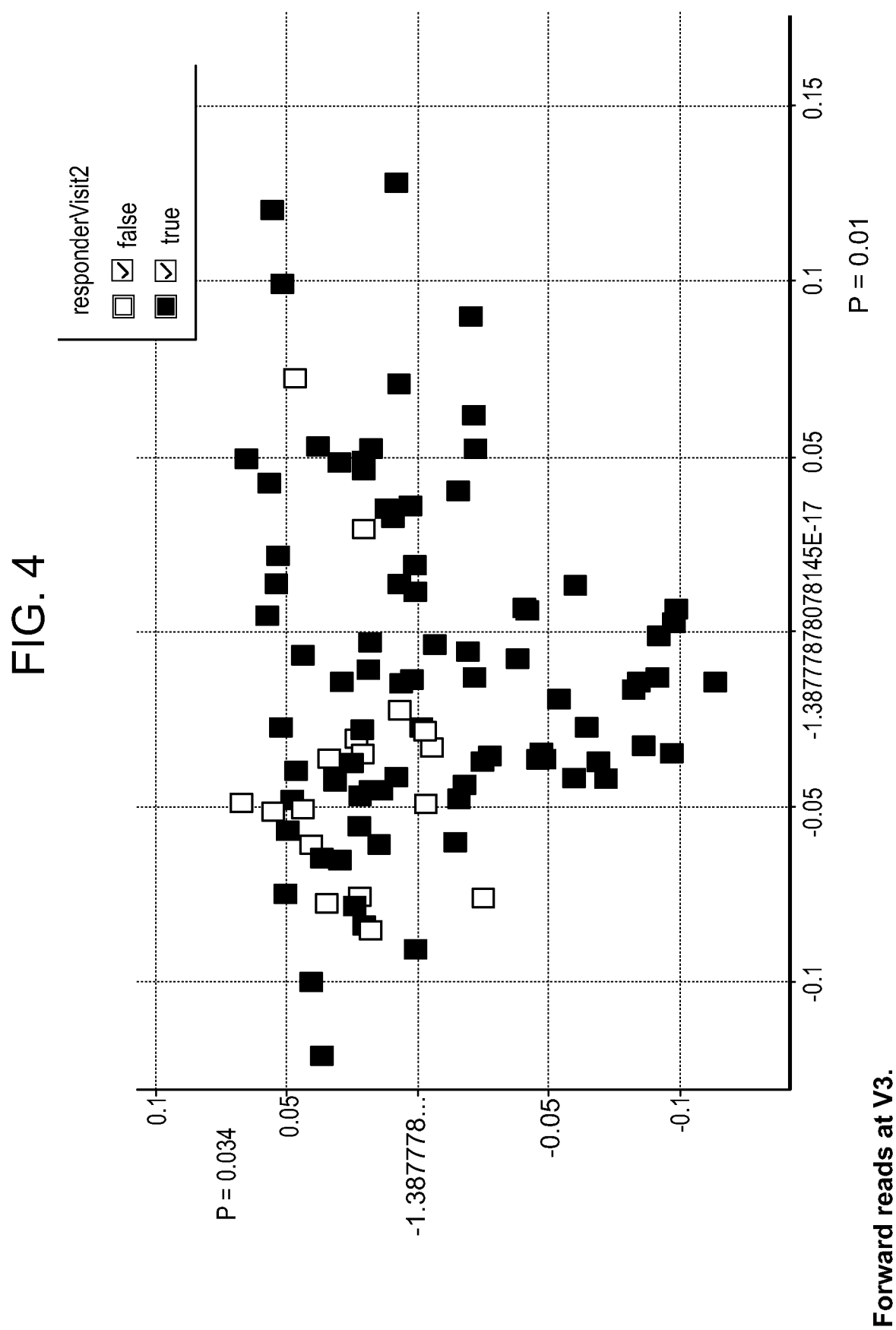
FIG. 4 shows samples from one of the paired end reads at V3.
Figure 5:
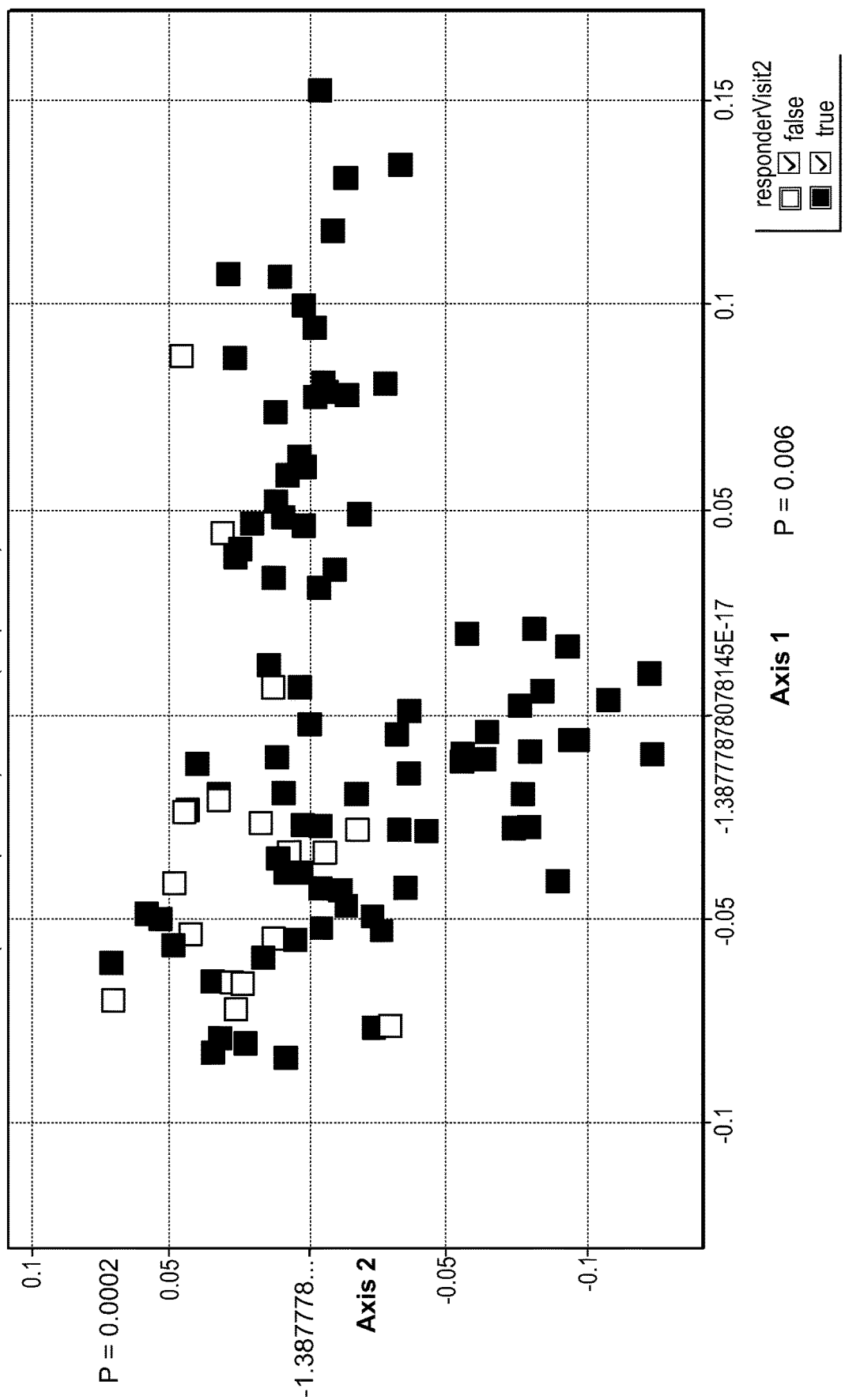
FIG. 5 shows samples from one of the paired end reads at V4.

In FIG. 3 there is clustering by responder/non-responder status.

Prior to treatment, responders have a lower diversity than non-responders. The depressed taxa are possible causes of IBS During treatment, rifaximin temporarily depresses diversity primarily by impacting low-abundance taxa. Rifaximin has been found to be effective in treating IBS. Surprisingly, we have found methods for predicting the subjects who will benefit from Rifaximin treatment for IBS.

Analysis of the microbial community is used herein as a predictor of responder status.

Based on the study, Table 1 shows the mean responder and nonresponder number by taxa. It is seen that where the mean responder number is higher than the mean nonresponder number are determined to be present, then the subject will respond to treatment. In certain embodiments, if the taxa in Table 1 wherein the mean responder number is lower than the mean nonresponder number are determined to be absent, then the subject will respond to treatment.

Thus, these taxa from Table 1, discriminate responders from non-responders from the V3 data.

TABLE 1

| Taxa | pValue | meanResponde | meanNon | sampleSiz | sampleSiz | adjustedP |
|---|---|---|---|---|---|---|
| *Sutterellaceae* | 0.000343 | 3.962389399 | 4.541995 | 84 | 17 | 0.034761 |
| *Sphingobacteriaceae* | 0.000355 | 2.056598811 | 1.415701 | 84 | 17 | 0.034761 |
| *Phyllobacteriaceae* | 0.000756 | 0.540212924 | 0.111546 | 84 | 17 | 0.042216 |
| *Thermoanaerobacteraceae* | 0.000992 | 0.252706886 | 0.508771 | 84 | 17 | 0.042216 |
| Burkholderiales_incertae_sed | 0.001154 | 0.258840648 | 0.907972 | 84 | 17 | 0.042216 |
| *Flavobacteriaceae* | 0.001292 | 2.928136665 | 2.441252 | 84 | 17 | 0.042216 |
| *Nocardiaceae* | 0.003107 | 0.514215239 | 0.154122 | 84 | 17 | 0.086995 |
| *Desulfomicrobiaceae* | 0.0041 | 0.158053086 | 0.414691 | 84 | 17 | 0.100439 |
| *Victivallaceae* | 0.007353 | 0.276397269 | 0.771497 | 84 | 17 | 0.160141 |
| *Succinivibrionaceae* | 0.008326 | 0.841664783 | 1.881286 | 84 | 17 | 0.16318 |
| *Moraxellaceae* | 0.010368 | 0.393517369 | 0.714397 | 84 | 17 | 0.184735 |
| *Prevotellaceae* | 0.015566 | 4.344658683 | 4.909328 | 84 | 17 | 0.254247 |
| *Clostridiaceae*.1 | 0.021914 | 3.145389304 | 3.397643 | 84 | 17 | 0.330393 |
| *Thermomicrobiaceae* | 0.028062 | 0 | 0.013409 | 84 | 17 | 0.365949 |
| *Pseudomonadaceae* | 0.030404 | 2.304621534 | 2.038307 | 84 | 17 | 0.365949 |
| *Burkolderlaceae* | 0.0315 | 0.518796744 | 0.283306 | 84 | 17 | 0.365949 |
| *Enterococcaceae* | 0.03174 | 1.564486253 | 2.184735 | 84 | 17 | 0.365949 |
| *Peptococcaceae*.1 | 0.036383 | 1.086486225 | 1.619638 | 84 | 17 | 0.396171 |
| *Veillonellaceae* | 0.058426 | 5.410740691 | 5.723877 | 84 | 17 | 0.602714 |

Figure 6:
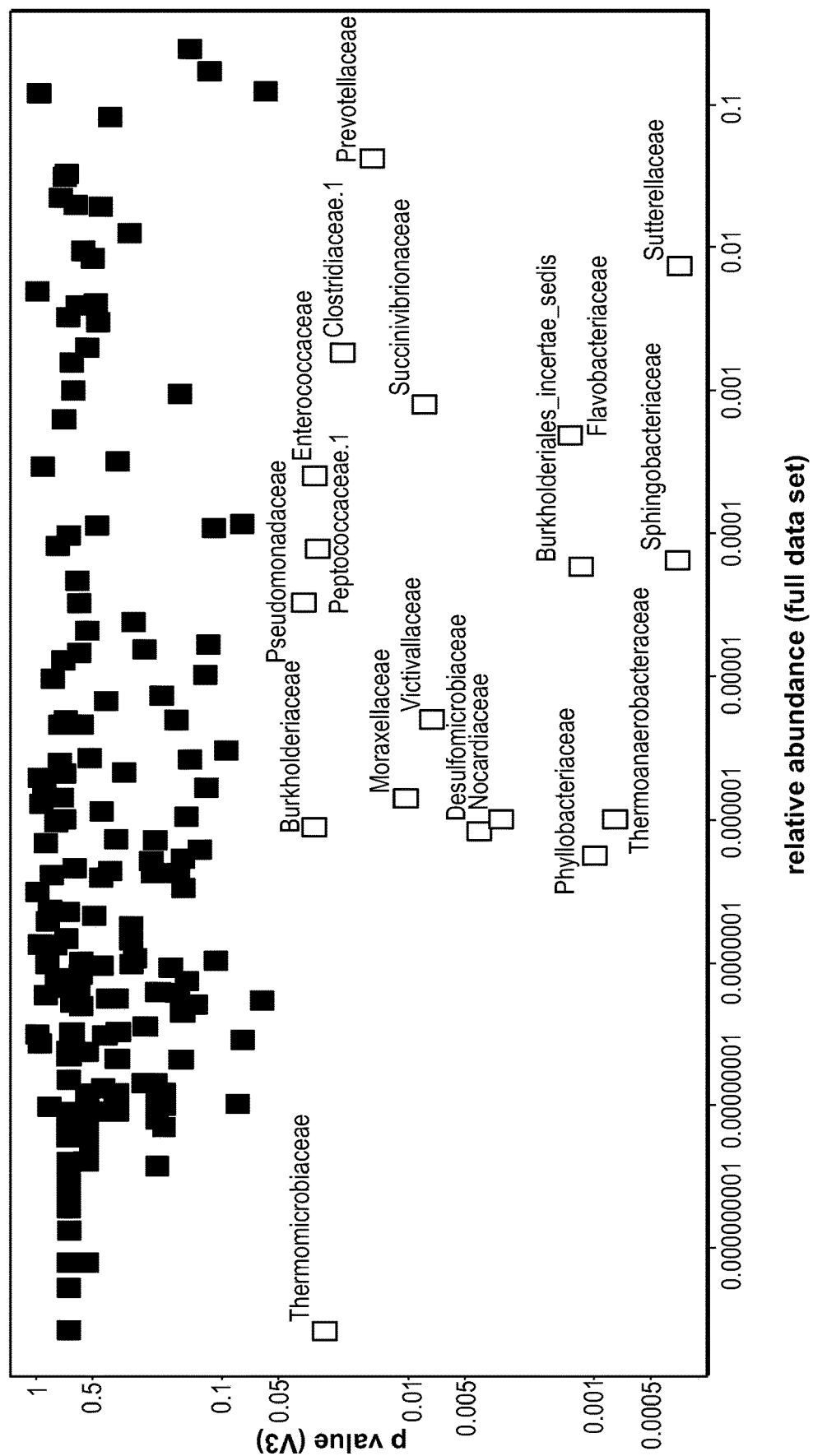
FIG. 6 shows the relative abundance of Table 1 markers.
Figure 7:
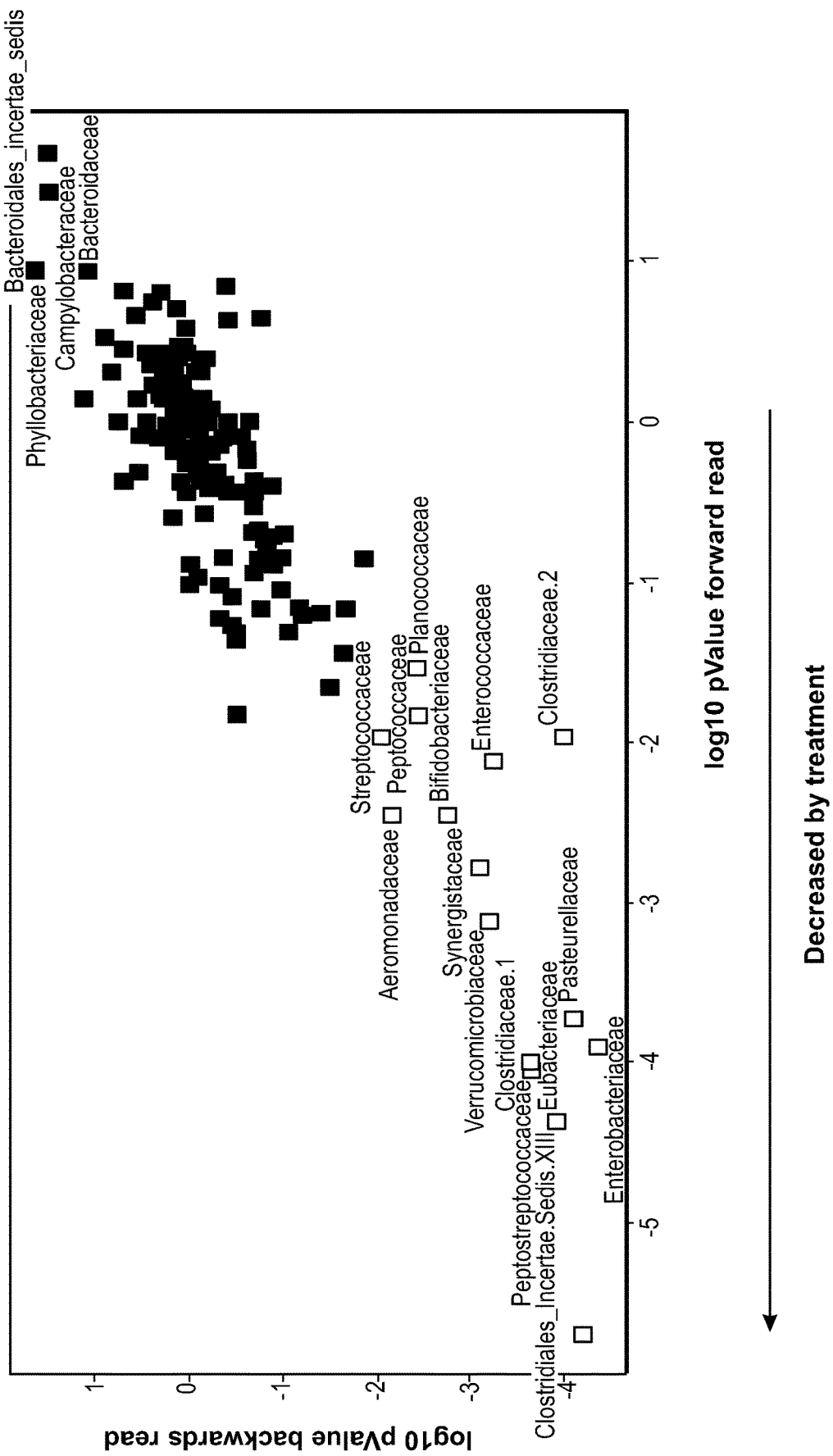
FIG. 7 shows what is different between V3 and V4 (n=100).
Figure 8:
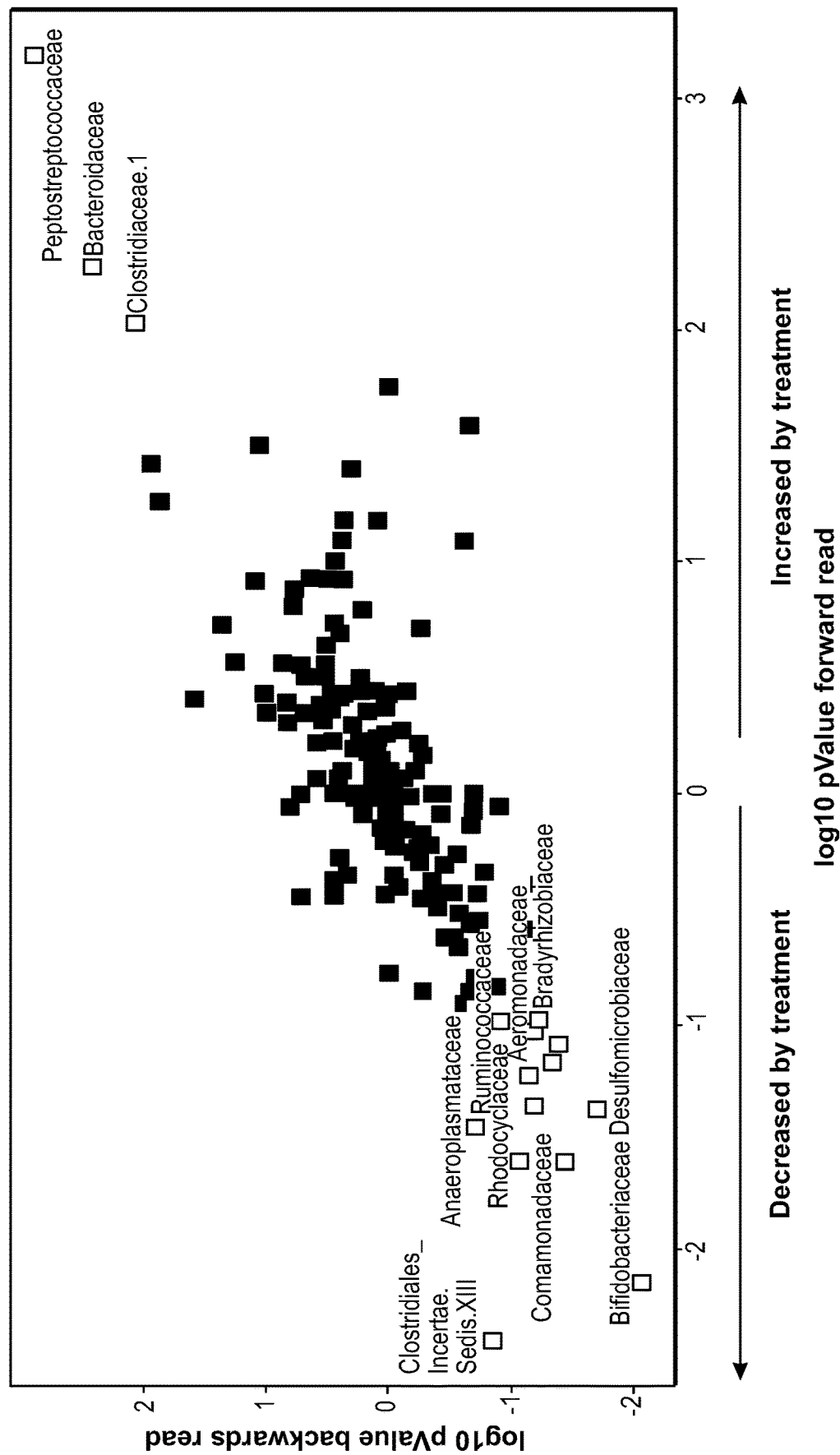
FIG. 8 shows that by using a paired Wilcoxon test to ask who is different between V3 and end of treatment (n=94), it can be shown that there is long-term resilience of the microbial community.
Figure 9:
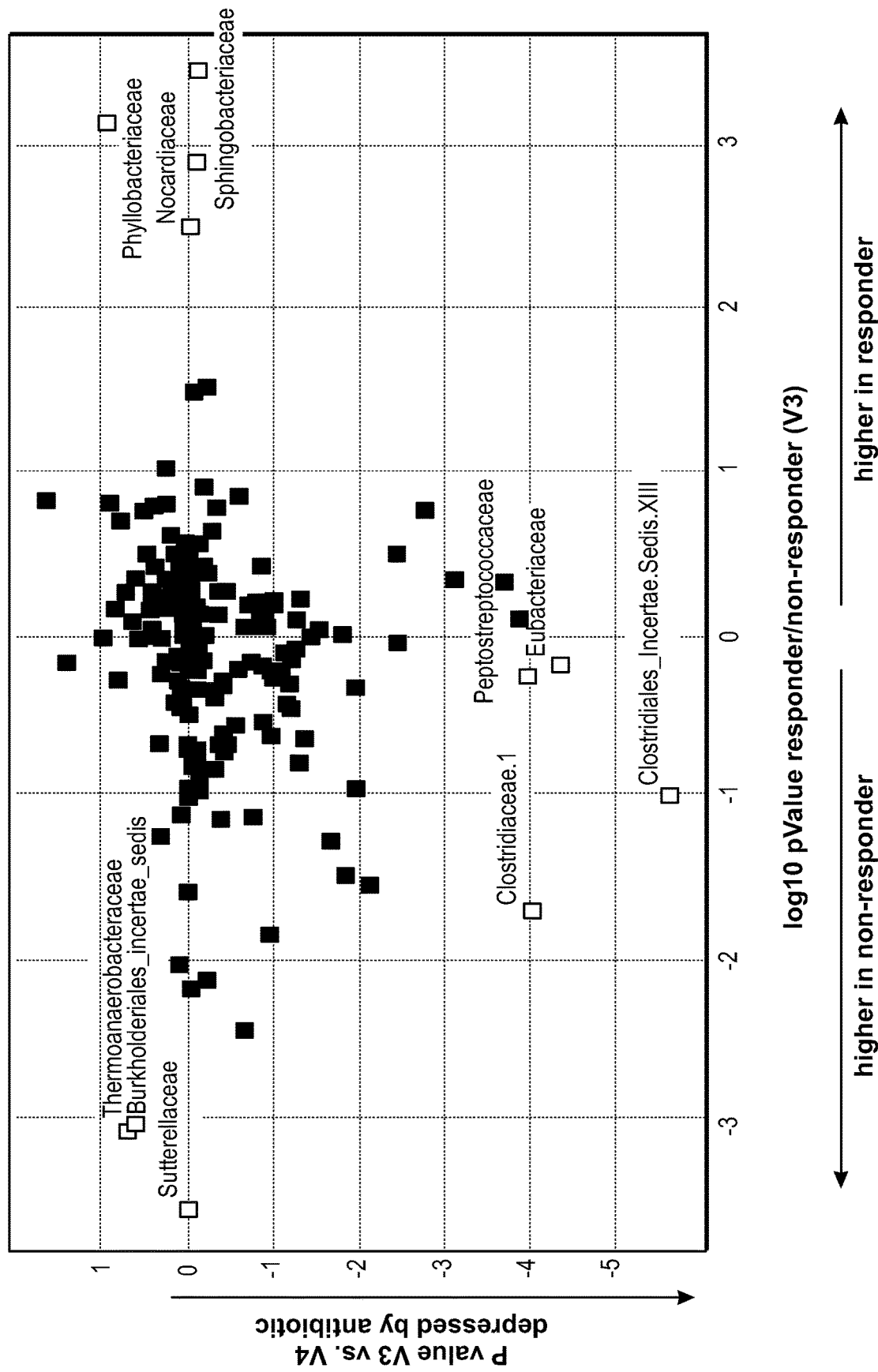
FIG. 9 shows that there is not a general relationship between bacteria suppressed by antibiotic and bacteria that predict responder.
Figure 10:
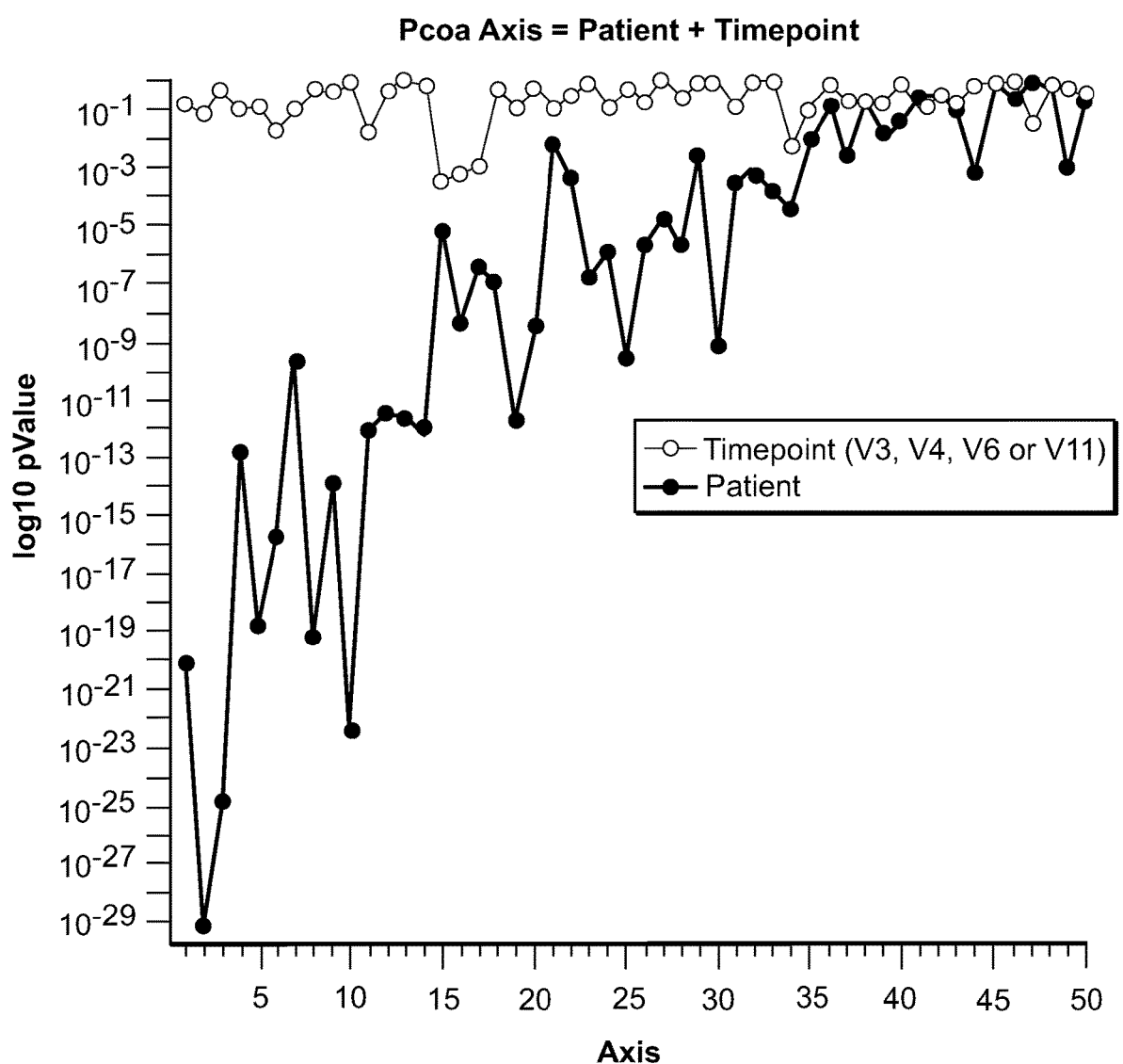
FIG. 10 shows the results of statistical modeling, which demonstrates that the microbial community is highly stable within individuals across rifaximin treatment time-points.

The markers are generally quite low abundance (See FIG. 6). Supervised classification was used to discriminate responders from non-responders from the V3 data.

In the study, there is data showing long-term resilience of the microbial community.

Example 2

GI Microbiota Characterization

In this study, we examined stool samples across all collection times in approximately 10% of the study population and characterized intestinal microbiota in terms of composition and diversity.

During the study, subjects provided stool samples at Visits 3 and 4 (baseline and after two weeks of open-label rifaximin 550 mg TID [Treatment 2], respectively), Visits 6 and 7 (prior to and immediately after two weeks of double-blind retreatment [Treatment 3] with rifaximin 550 mg TID or placebo), and Visit 11 (end of study). Bacterial DNA was isolated from fecal samples, and the V4 hyper-variable region of the 16S rRNA gene is amplified using two-step PCR with Illumina HiSeq2000 sequencing technology.

The sequencing reactions were designed so that the forward and backward paired Illumina reads did not overlap. Forward and backward reads will therefore be treated as technical replicates with independent analyses performed in our pipeline to ensure that our conclusions are not dependent on the utilization of any particular sub-region of the 16S rRNA gene.

All non-microbial sequences, sequences with low quality scores and sequences that did not have an exact match to an expected primer sequence were removed. Sequences were analyzed by two methods. The program AbundantOTU will be utilized to perform de-novo clustering of sequences in a way that is not dependent on a database.

The effects of rifaximin on the gut microbiota in the IBS-D repeat treatment study, TARGET 3, were evaluated by two methods: traditional culture techniques and next-generation gene sequencing of stool samples collected from approximately 100 randomly selected subjects in the trial. Skin swabs were also obtained from an additional 113 randomly selected subjects and cultured for *Staphylococcus* bacteria.

Using next-generation 16S rRNA gene sequencing methods, we generated approximately 2.2 billion base pairs from stool samples collected over the course of the study from approximately 100 randomly selected subjects. The data reveal no disturbance of fecal microbiota, based on both diversity (see Table 2) and Bray-Curtis similarity (see Table 3) measures, in subjects taking repeat courses of rifaximin as compared to subjects taking a single course of rifaximin followed by placebo for the remainder of the trial.

TABLE 2

Change from Randomization in Shannon Diversity Index by Timepoint and Treatment Group during Double-Blind Period (Population: ITT)

| Timepoint/Statistics | DB Placebo | DB Rifaximin 550 mg TID | P-value |
|---|---|---|---|
| Randomization | | | |
| n | 35 | 34 | |
| Week 2 | | | |
| n | 35 | 37 | |
| Change from Randomization to WEEK 2 | | | |
| n | 34 | 34 | 0.4329 |
| WEEKS 10-22 | | | |
| n | 8 | 5 | |
| Change from Randomization to WEEKS 10-22 | | | |
| n | 8 | 4 | 0.3444 |
| WEEK >=23 | | | |
| n | 25 | 28 | |
| Change from Randomization to WEEK >=23 | | | |
| n | 24 | 26 | 0.4972 |

TABLE 3

Summary of Bray-Curtis Similarity Compare to randomization in Faecal Microbiota by Timepoint and Treatment Group during Double-Blind Period (Population: ITT)

| Timepoint/Statistics | DB Placebo | DB Rifaximin 550 mg TID | P-value |
|---|---|---|---|
| Week 2 | | | |
| n | 34 | 34 | 0.876 |
| WEEKS 10-22 | | | |
| n | 8 | 4 | 0.7275 |
| WEEK >=23 | | | |
| n | 24 | 26 | 0.5436 |

Results of the culture and susceptibility testing demonstrate no evidence of cross-resistance to non-rifamycin antibiotics in isolates grown from either stool or skin swab cultures. Repeat treatment courses of rifaximin do not appear to predispose patients to the emergence of potentially pathogenic bacteria (e.g., *C. difficile, Enterococcus*, or *Staphylococcus*) in the stool or on the skin. Given the high concentration of rifaximin achieved in the stool, transient changes in the rifaximin minimum inhibitory concentrations (MICs), a measure of microbial sensitivity to an antibiotic, were observed in some of the normal flora but these changes were reversible over time. A very small number of *C. difficile* isolates were identified in stool samples at a rate consistent with literature reports of asymptomatic carriers in the general population, and none of these isolates demonstrated rifaximin resistance.

This is the most comprehensive microbiome data set in IBS patients to date with more than two billion data points collected. Longitudinal samples demonstrate microbiome stability (See Figure a) with repeat rifaximin dosing and alterations in antibiotic susceptibility for potential major pathogens were not apparent with repeat rifaximin use.

Example 3

GI Bacterial Culture and Resistance

In this study, (See study design of FIG. 1) we examined stool samples across all collection times in the study population, and we also characterized the susceptibility of the stool microbiota, including Gram-negative rods and *C. difficile*, to antibiotics of clinical interest. Stool samples were collected as described for the microbiota study.

Stool aliquots from the selected subjects were inoculated onto tryptic soy agar plates with 5% sheep's blood to identify aerobic organisms. Aerobic plates were incubated at 34-36° C. with 5-7% CO2 for 24 hours or under desired conditions. Stool aliquots for anaerobic organisms were inoculated onto cycloserine ceftoxitin fructose agar or *Bacteroides* bile esculin agar for selection of *C. difficile* and *Bacteroides* species. Anaerobic plates were inoculated under anaerobic conditions with an additional sample inoculation from the stool sample. Anaerobic plates were incubated at 34-36° C. under anaerobic conditions (eg, anaerobic chamber) for 48 hours.

The stool sample was inoculated on the first quadrant of the agar plate with the subject's specimen. Using standard means of inoculation, the specimen was streaked across interconnecting quadrants of the agar plate in order to isolate the bacterial colonies. The agar plates were evaluated for growth using semi-quantitative criteria of 1+, 2+, 3+ and 4+. The criteria were defined in connection with the quartile divisions of the inoculated agar plates. Aerobic isolates were tested for susceptibility to a panel of antibiotics using the broth microdilution method. Anaerobic isolates were tested for susceptibility to a panel of antibiotics using the agar dilution method.

Each bacterial species isolated and tested for antibiotic susceptibility was grouped into a larger class, i.e., Enterobacericeae, Enterococcaceae, Bacteroidaceae, Staphylococcaceae, Clostridiaceae, or Pseudomonadaceae. The Enterobactericeae investigated included members of the *Escherichia, Klebsiella, Proteus, Enterobacter*, and *Citrobacter* species. The MIC data from each subject in a treatment group (Double Blind (DB) placebo, DB rifaximin, Open-Label (OL) rifaximin) were compiled by visit in order to determine the MIC range for the treatment population. The MIC concentration at which ≥50% of the isolates were inhibited was the MIC50 for the population. The MIC90 value represented the MIC value at which ≥90% of the population was inhibited.

For all antibiotics with CLSI defined breakpoints for a particular bacterial species (M100-S24), MIC values were interpreted using those breakpoints. However, for this analysis, if an antibiotic had defined sensitive and intermediate categories, both were classified as sensitive. If breakpoints had not been established for an antibiotic but the antibiotic product label indicated ranges for in vitro susceptibility, those values were used to categorize the MICs. In all other cases, MIC values at or above the highest dilution tested in the MIC panel were considered resistant, and MIC values below the highest dilution were considered sensitive.

The bacteria isolated from the stool samples tested in RFIB3053 are summarized below.

Gram Negative
*E. coli*
*Klebsiella* spp.
*Pseudomonas* spp.
*Enterobacter* spp.
*Serratia* spp.
*Proteus* spp.
*Bacteroides* spp.

Gram Positive
*Enterococcus* spp.
*Staphylococcus* spp.
*Clostridium difficile*

Sensitivity testing was performed by broth microdilution for aerobic bacteria and by agar dilution for anaerobic bacteria using the following antibiotics:
Rifaximin—anaerobes
Rifampin—anaerobes
Vancomycin—anaerobes
Fidaxomicin—anaerobes
Metronidazole—anaerobes
Rifaximin—aerobes
Rifampin—aerobes
Ceftazidime—aerobes
Ceftriaxone—aerobes
Ciprofloxacin—aerobes
Imipenem—aerobes
Meropenem—aerobes
Pipercillin/Tazobactam—aerobes The predominant bacteria families isolated from stool cultures isolated were Bacteroidaceae (525 isolates, representing 36.7% of the total isolates), Enterobacteriaceae (484 isolates representing 33.9% of total isolates), and Enterococcaceae (286 isolates, representing 20% of the total isolates). Across visits, regardless of treatment group, 22 isolates of *C. difficile* were cultured from stool. *C. difficile* represented 1.5% of the total cultured bacteria. *Staphylococcus* isolates represented only about 6.4% of the total isolates.

Subjects who enrolled in the OL phase of the study and received Treatment 2 had a total of 336 isolates that were cultured from stool on Day 1. The Enterobacteriaceae (124 isolates) and Bacteroidaceae (122 isolates) families accounted for the majority of the isolates. *Staphylococcus* represented 18 of the total isolates on Day 1 (5.4%). Four isolates of *C. difficile* were identified on Day 1. This proportion of isolates remained consistent throughout the OL phase, with *C. difficile* and *Pseudomonas* isolates being rare and sporadically cultured across visits.

On Day 1 of the DB phase, 113 isolates were identified from stool from subjects enrolled in the placebo group, and 131 isolates were identified from subjects enrolled in the rifaximin treatment group. As with the OL phase, bacteria from the Bacteroidaceae and Enterobacteriaceae families represented the majority of isolates cultured from stool in both groups. Two *C. difficile* isolates were found in placebo treated subjects on Day 1, with 4 *C. difficile* isolates identified in subjects randomized to receive rifaximin at Day 1. After 2 weeks of treatment with either rifaximin or placebo, similar numbers of bacteria were isolated in the 2 treatment groups. There were 2 *C. difficile* isolates recovered from the stool of placebo treated subjects and 1 isolate recovered from rifaximin treated subjects at Week 2. Throughout the follow up period, the relative percentages of isolates were consistent with those observed on Day 1 and Week 2. No *C. difficile* isolates were found in rifaximin treated subjects in the follow up period, while 5 *C. difficile* isolates were cultured from placebo treated subjects in the follow-up period.

There were seven strains of yeast isolated from 14 subjects, with a total of 17 yeast isolates. Overall, yeast cultures represented 1.2% of the cultures isolated from stool (1429 total cultures including bacteria and yeast). Four of the isolates were cultured from the Treatment 2 samples taken prior to rifaximin treatment. Only one subject had yeast isolated at more than one visit.

Rifaximin treatment in the study described herein appeared to have little effect on the stool microbiota in terms of both the ability to culture organisms and susceptibility to rifaximin, rifampin and nonrifamycin antibiotics. Except for some minor changes in the number of organisms cultured across treatment groups, there was no appearance of overgrowth with rifaximin treatment. Additionally, there were minimal yeast isolates cultured from stool, consistent with normal carriage patterns.

Transient increases in the MIC values for rifaximin and rifampin were observed with *Staphylococcus* isolates cultured from stool. The increases in the MIC were observed at the end of Treatment 2 of the OL phase and at the end of Treatment 3 in the DBR phase. In follow-up visits, which were binned into groups according to when subjects returned, the MIC of *Staphylococcus* returned to baseline as the time since the last rifaximin treatment increased. While there were some increases in the MIC50 or MIC90 of rifaximin against some species, e.g., *Bacteroides*, the increases were within the range of MICs reported both at baseline. With the Enterobacteriaceae family, the MIC50 increased by 1 to 2 dilutions in RFIB3053, with a rapid recovery to baseline susceptibility levels. This rapid recovery in the stool is consistent with reports of rapid disappearance of rifaximin-resistant bacteria from stool, particularly aerobic bacteria, which seemed to recover quickly. Along with the minimal changes in MIC observed, there were no increases in the numbers of potential pathogens that were cultured from stool. No treatment related effects were apparent in the susceptibility of stool bacteria to other antibiotics, which is to be expected given the mechanism of resistance to rifaximin Rifaximin and other rifamycin antibiotics are inhibitors of bacterial RNA synthesis, which acts by binding to the beta-subunit of bacterial DNA-dependent RNA polymerase. The known mechanism of bacterial resistance to the rifamycin class, mutations of the gene encoding the polymerase, is chromosomal mediated rather than plasmid mediated. The mutations are known to occur at highest frequency in two specific loci of the rpoB gene and result in a resistant but sub-optimally functioning enzyme. Therefore, cross-resistance to other antibiotic classes is limited by a lack of plasmid transfer, and rifaximin has a low risk of spreading resistance to non-rifamycin antibiotics.

In the study described herein, there were only transient resistance to *Staphylococcus* species identified in cultures from stool samples, and no cross resistance to non-rifamycin antibiotics was observed. The transient increases in MIC values for rifaximin and rifampin recovered quickly when rifaximin treatment was discontinued, supporting evidence of a lack of fitness of the mutation without drug pressure. There was no evidence of rifaximin mediated cross resistance to any non-rifamycin antibiotic tested for any of the bacteria that were cultured in stool. Additionally, while there were transient increases in the MIC of *Staphylococcus* cultured in stool, they were reversible with time. Sensitivity of other bacteria did not seem to be affected by rifaximin treatment. There were no increased infection rates following single or repeat treatment courses with rifaximin in IBS patients, as consistent with the long-term safety and efficacy of rifaximin for treatment of IBS.

Rifaximin treatment leads to a transient increase in MIC against *Staphylococcus*. This increase in MIC recovers quickly after rifaximin treatment is discontinued, and is therefore not sustained long term. In other words, rifaximin does not have a long term effect on the microbiota susceptibility to it or other antibiotics. It was surprisingly found that Rifampin MICs and changes in MIC paralleled those of rifaximin in repeat treatment. Overall, in both the OL and DB phases of the study, rifampin had transient elevations in MIC and resistance to bacteria such as *Staphylococcus* that recovered with discontinuation of rifaximin treatment. Patterns with other antibiotics were not observed.

Provided herein is the prospective evaluation of stool culture and antibiotic susceptibility data from the phase 3 study. From this data, it is demonstrated that overall, there was no evidence of increased levels of pathogens such as *Clostridium difficile* compared to placebo in the stool samples cultured from the subjects. All *C. difficile* cultured was highly susceptible to rifaximin during susceptibility testing. There was no evidence of rifaximin-mediated cross resistance to any non-rifamycin antibiotic tested for any of the bacteria that were cultured in stool. While there were transient increases in the rifaximin minimum inhibitory concentrations of *Staphylococcus* cultured in stool, they were reversible with time. Sensitivities of other bacteria were not affected by rifaximin treatment.

It was surprisingly found that repeat treatment courses of rifaximin do not predispose patients to the emergence of potentially pathogenic bacteria (e.g., *C. difficile*, *Enterococcus*, or *Staphylococcus*) in the stool. A very small number of *C. difficile* isolates were identified in stool samples at a rate consistent with literature reports of asymptomatic carriers in the general population, and none of these isolates demonstrated rifaximin resistance. Given the high concentration of rifaximin achieved in the stool, transient changes in the rifaximin minimum inhibitory concentrations (MICs), a measure of microbial sensitivity to an antibiotic, were observed in some of the normal flora but these changes were reversible over time.

Example 4

Skin Swab

In this study of patients with Irritable Bowel Syndrome with Diarrhea (IBS-D), we characterized the growth and antibiotic susceptibility of *Staphylococcus* strains cultured from skin swab samples in patients with IBS-D.

For the skin swab study, skin swab collection was performed for a subset of subjects (approximately 10% of the study population) at each of the following visits: Visits 3 and 4 (baseline and after two weeks of open-label rifaximin 550 mg TID [Treatment 2], respectively), Visits 6 and 7 (prior to and immediately after two weeks of double-blind retreatment [Treatment 3] with rifaximin 550 mg TID or placebo), and Visit 11 (End of Study). For each subject in this study, skin swabs were collected from the peri-rectum, nares, palms of hands, and forearms, and swabs were shipped immediately to the microbiology laboratory at ambient temperature in media-containing tubes. Skin swab cultures were conducted to isolate all *Staphylococcus* species.

During the Open Label (OL) rifaximin period (Treatment 2), all subjects received rifaximin. Subjects who responded to rifaximin treatment were eligible for the double-blind (DB) retreatment phase of the study. To evaluate the effects of a single treatment of rifaximin without the complications of potential retreatment, for subjects who enrolled in the DB phase of the study, their skin swab sample from the start of Treatment 3 served as an "end of study" sample for the open-label phase of the study.

Subjects who enrolled in the DB phase of the study were randomized to receive either rifaximin or placebo. Subjects were compared at the Treatment 3 visit, EOT3 visit and EOS visit.

Swabs were collected using the following procedures:
Skin of left lower arm and right lower arm: The lower arm was swabbed with a single swab, using approximately 10 total strokes. The swab was rotated with each stroke so that all sides of the swab were exposed to the skin. There was one swab used for each arm.
Palms of hands: The full palm of the hand was swabbed, rotating the swab so that all sides were exposed to the skin. Both palms were swabbed with the same swab.
Nares: The tip of the swab was carefully inserted into each nare and twisted twice. Care was taken to ensure that the swab was not inserted far into the nares, as the swab was intended to sample the external nares only. The swab was not inserted past ~¼ inch for each nare. Both nares were sampled with the same swab.
Peri-rectum: The swab was swiped around the rectal area and rotated with each stroke to ensure that all sides of the swab were exposed to the skin. The swab was not inserted into the rectum and was swabbed around the outside of the rectum only.

Upon receipt at the microbiology laboratory, each skin swab was plated onto tryptic soy agar containing 5% sheep's blood and Columbia-colistin nalidixic acid agar with 5% sheep's blood to select for Gram-positive colonies. The specimen swab was inoculated on the first quadrant of the agar plate. Using standard means of inoculation, the specimen was streaked across interconnecting quadrants of the agar plate in order to isolate the bacterial colonies. The inoculated plates were incubated at 35° C. in a 5-7% $CO_2$ incubator, with plates examined at 24 and 48 h for bacterial growth. The agar plates were evaluated for growth using semi-quantitative criteria of 1+, 2+, 3+ and 4+. The criteria were defined in connection with the quartile divisions of the inoculated agar plates.

Culture and Susceptibility Testing of Skin Swab Isolates

*Staphylococcus* isolates were tested for susceptibility to a panel of antibiotics using the broth microdilution method. For Minimum Inhibitory Concentration (MIC) determination, approximately 3 to 5 isolated colonies were selected from sub-cultured plates to create a suspension approximating a 0.5 McFarland standard according to CLSI guidelines. The bacterial suspension was prepared immediately prior to inoculation of incubation plates. Stocks of the antibiotics were prepared and then diluted into cation adjusted Mueller-Hinton broth. Each test plate was incubated at 35±1° C. in CO2 for the appropriate amount of time. Quality control strains were included with testing plates as appropriate. Purity control plates and positive and negative growth controls were included with each sample run.

Sensitivity testing was performed by broth microdilution using the following antibiotics:
Rifaximin
Rifampin
Ceftazidime
Ceftriaxone
Cephalothin
Ciprofloxacin
Imipenem
Meropenem
Piperacillin
Tazobactam
Trimethoprim
Sulfamethoxazole
Vancomycin In the OL phase of the study, 1115 staphylococcal isolates were identified from skin swabs collected from subjects who participated in the skin swab study (113 subjects). At the Treatment 2 Visit (Day 1), prior to initiation of OL rifaximin, 373 isolates were cultured, and at the EOT2 Visit (Week 2), 336 staphylococcal isolates were cultured. The most abundant species of *Staphylococcus* identified from skin swabs was *S. epidermidis*, which represented 55% of the total isolate count. A total of 52 isolates of *S. aureus* were identified in the OL phase of the study (4.7% of all isolates in OL phase). Of these isolates, 22 were cultured at Day 1, 11 were cultured at Week 2, and the remaining 19 were cultured during the follow-up period. With regards to location, the majority of isolates across visits were cultured from the nares and the peri-rectum skin.

In the Double Blind (DB) repeat treatment phase of the study, 171 staphylococcal isolates were cultured from 12 subjects randomized to receive placebo and 208 staphylococcal isolates were cultured from 18 subjects randomized to receive rifaximin. There were 81 *S. epidermidis* and 9 *S. aureus* isolates identified from placebo treated subjects, and 114 *S. epidermidis* and 17 *S. aureus* isolates identified from rifaximin treated subjects. With regards to location, the majority of isolates across visits were cultured from the nares and the peri-rectum skin.

MIC Analysis for Rifaximin

Subjects who enrolled in the OL only phase of the study and received only Treatment 2, had a total of 373 staphylococcal isolates that were cultured at the Treatment 2 visit (Day 1). The rifaximin $MIC_{50}$ value for the staphylococcal isolates at Treatment 2 was 0.015 µg/mL, and the $MIC_{90}$ value was 0.03 µg/mL. At the EOT2 Visit (Week 2), the $MIC_{50}$ for rifaximin was 0.015 µg/mL, but the $MIC_{90}$ value increased to 32 µg/mL. The overall range of MIC values was wider at the Week 2 Visit, from ≤0.001 µg/mL to 128 µg/mL. With the OL Last Assessment Visits, which occurred between Week 7 and Week 32, the $MIC_{90}$ value for rifaximin lowered from 2 µg/mL during Weeks 7 to 10, to an $MIC_{90}$ value of 0.03 µg/mL from Week 11 onward. The range of MIC concentrations became more narrow with time off of rifaximin treatment, with the maximum MIC concentration observed decreasing from 64 µg/mL to 0.06 µg/mL.

On Day 1 of the DB phase (Treatment 3), 48 staphylococcal isolates were recovered from the 12 subjects randomized to receive placebo that participated in the skin swab study, with a rifaximin $MIC_{50}$ value of 0.015 µg/mL and an $MIC_{90}$ value of 0.03 µg/mL. These values remained consistent throughout the remainder of the study, demonstrating that there was no long term effect of rifaximin treatment on staphylococcal isolates susceptibility to rifaximin.

The range of MICs at Day 1 was wide (≤0.001 µg/mL to 64 µg/mL), due at least in part to the fact that subjects were previously treated with rifaximin in OL Treatment 2, and may have enrolled in DB Treatment 3 before the staphylococcal isolates had fully returned to pretreatment susceptibility. For all of the DL Last Assessment Visits (occurring between Week 11 and Week 38), the MIC range for rifaximin narrowed (0.004 µg/mL to 0.06 µg/mL). For the skin swab subjects randomized to receive rifaximin in the DB phase of the study (18 subjects), on Day 1, the initial $MIC_{50}$ and $MIC_{90}$ values were 0.015 µg/mL and 0.03 µg/mL, respectively, showing no difference from the placebo treated group. At the EOT3 Visit (Week 2), the $MIC_{90}$ value for rifaximin was 32 µg/mL. With the DB Last Assessment Visits, the $MIC_{50}$ value remained low (0.015 to 0.06 µg/mL), while the $MIC_{90}$ remained elevated. For the subjects sampled between Week 11 and Week 14, the $MIC_{90}$ was 64 µg/mL. The $MIC_{90}$ value decreased to 0.5 µg/mL between Week 15 to Week 22, and was 0.06 µg/mL for subjects who were sampled between Week 23 and Week 38. After receiving up to three treatments of rifaximin, staphylococcal isolates did not exhibit sustained elevation in rifaximin MIC values.

MIC Analysis for Rifampin

Rifampin MICs were analyzed based on the CLSI defined breakpoints for *Staphylococcus*, where MIC≥4 µg/mL was considered resistant. For the purpose of the analysis, all MIC values <4 µg/mL were considered susceptible to rifampin. Subjects who enrolled in the OL phase of the study had a MIC range of ≤0.015-0.12 µg/mL on Day 1 of Treatment 2, with $MIC_{50}$ and $MIC_{90}$ of ≤0.015 µg/mL at the Treatment 2 visit, prior to treatment with rifaximin. Following treatment with rifaximin, at Week 2, there were 39 isolates with a MIC value ≥4 µg/mL, and 297 isolates with an MIC value of <4 µg/mL. Rifampin resistant isolates were located primarily on the peri-rectum (32 resistant isolates), with 4 resistant isolates cultured from the palms of the hands and 3 resistant isolates cultured from the left lower arm swabs. The $MIC_{50}$ at EOT2 was ≤0.015 µg/mL, with an $MIC_{90}$ of 16 µg/mL. At the OL Last Assessment Visits that occurred between Week 7 and Week 32, 16 of 406 total staphylococcal isolates had a rifampin MIC value of ≥4 µg/mL. During Weeks 7 to 10, the $MIC_{90}$ for rifampin was 0.5 µg/mL, which decreased to ≤0.015 µg/mL from Week 11 onward. Seven rifampin resistant isolates (9.5% of isolates) were isolated from skin swab samples between Week 7 to Week 10, with the majority of the resistant isolates localized to the peri-rectum. Between Week 11 and Week 14, 7 resistant isolates were cultured from skin swabs (2.8% of isolates). No rifampin resistant isolates were observed in skin swab samples from Week 15 to Week 32.

Subjects who received placebo treatment in the DB phase had rifampin $MIC_{50}$ and $MIC_{90}$ values of ≤0.015 µg/mL at all Visits, from Day 1 (Treatment 3) to the DB Last Assessment Visits. As with rifaximin, the maximum observed MIC value for rifampin was elevated at the Day 1 and Week 2 Visits, which may be attributable to incomplete return to susceptible levels prior to randomization in the DB phase. For placebo treated subjects, there were 3 rifampin resistant isolates during the treatment period: 1 isolates at Day 1 and 2 isolates at Week 2, all from the peri-rectum.

With the other antibiotics, regardless of the treatment group (OL rifaximin, DB placebo, or DB rifaximin), there were no patterns to the MIC changes in RFIB3053. Some *Staphylococcus* isolates demonstrated low levels of resistance to antibiotics, such as ciprofloxacin, that did not substantially change with rifaximin treatment or time.

Transient shifts in the MIC for rifaximin and rifampin were observed with single and repeat treatment with rifaximin. The increases in MIC were not sustained over a long period of time and subjects had a skin staphylococcal flora that returned to susceptible levels by the end of study. Most resistant isolates were found on the peri-rectum with minimal resistant isolates on hands forearms, palms or nares.

Other antibiotics tested did not exhibit changes in MIC that could be caused by rifaximin treatment.

Results of the culture and susceptibility testing demonstrate no evidence of cross-resistance to non-rifamycin antibiotics in isolates grown from either stool or skin swab cultures. Repeat treatment courses of rifaximin do not appear to predispose patient to the emergence of potentially pathogenic *Staphylococcus* strains on the skin.

Repeat treatment courses of rifaximin do not appear to predispose patients to the emergence of potentially pathogenic bacteria (e.g., *C. difficile, Enterococcus,* or *Staphylococcus*) in the stool or on the skin. A very small number of *C. difficile* isolates were identified in stool samples at a rate consistent with literature reports of asymptomatic carriers in the general population, and none of these isolates demonstrated rifaximin resistance. Given the high concentration of rifaximin achieved in the stool, transient changes in the rifaximin minimum inhibitory concentrations (MICs), a measure of microbial sensitivity to an antibiotic, were observed in some of the normal flora but these changes were reversible over time.

Overall, the data from skin swab cultures indicate that treatment with rifaximin does not lead to clinically significant antibiotic resistance. No cross-resistance with other antibiotics tested was observed. There were no changes in MIC50 values for rifaximin or rifampin. Transient changes in MIC90 values for rifaximin and rifampin for staphylococcal isolates were observed, and return to baseline values was observed by the end of the study. These transient changes would not be anticipated to result in interference with clinical practice, because neither rifaximin nor rifampin is a first line treatment for staphylococcal infections. Additionally, no increase in the number of *S. aureus* isolates was observed in the OL or DB phases of the study, and no *S. aureus* isolates showed resistance to rifaximin or rifampin.

Example 5

Study Design

The overall study design for the phase 3 trial is shown in FIG. 1.

Subjects entered a Screening/Treatment 1 Phase which included a 10 (±3) day treatment, during which the subjects received single-blind placebo TID and completed a daily symptom diary. Following the Screening/Treatment 1 Phase, eligible subjects entered the Treatment 2 Phase and received open-label rifaximin 550 mg TID for 2 weeks with a 4 week treatment-free follow-up. At the end of the Treatment 2 Phase, subjects who achieved treatment success in both IBS-related abdominal pain and stool consistency during at least 2 weeks of the 4 week follow-up period were classified as responders and entered a treatment-free Maintenance Phase 1. Non-responders in the Treatment 2 Phase were withdrawn from the study to provide an enriched population of subjects who respond to treatment with rifaximin.

The treatment-free Maintenance Phase 1 varied in time (up to 18 weeks in total) and depended upon the time of symptom recurrence. Subjects who did not meet recurrence criteria by the end of the Maintenance Phase 1 were withdrawn from the study. Subjects with recurrence entered Treatment 3 Phase, also referred to as the Double-Blind (DB) Repeat Treatment Phase. In this phase, subjects were randomized 1:1 to receive either rifaximin 550 mg TID or placebo TID for 2 weeks with a 4-week treatment-free follow-up. All subjects from the Treatment 3 Phase then entered a 6-week maintenance phase (Maintenance Phase 2). All subjects from Maintenance Phase 2 then entered a Second Repeat Treatment (SRT) Phase (i.e., Treatment Phase 4) where they received the same treatment as previously assigned in the Treatment 3 Phase (rifaximin 550 mg TID or placebo TID) for 2 weeks with a 4-week treatment-free follow-up. Following the end of the SRT phase, all subjects underwent an additional 4-week, treatment-free follow-up with a concluding end-of-study (EOS) visit.

In FIG. 1, the stool collection time points are denoted in dark grey boxes. All subjects participating in RFIB3053 provided stool samples at the Treatment 2 (T2) Visit, End of Treatment 2 (EOT2) Visit, Treatment 3 (T3) Visit, EOT 3 Visit, and End of Study (EOS) Visit. The follow-up period was variable for subjects; therefore, for purposes of data analysis and interpretation, the follow-up visits were binned into 4-week periods in order to determine whether there was an effect on time on antibiotic susceptibility of staphylococcal isolates.

Additionally, if subjects had a recurrence of symptoms and enrolled in the DB phase of the study, the Treatment 3 visit was treated as the final visit of the OL treatment phase. The Treatment 3 visit also served as the DB baseline visit for subjects who enrolled in the DB phase of the study.

16S rRNA Gene Sequencing:

Stool aliquots from the selected subjects were shipped frozen for genomic sequencing. The samples were thawed at the time of testing. DNA was extracted from stool. Next-generation sequencing technology (Illumina HiSeq2500) was used to sequence the V4 region of the 16S ribosomal RNA. In order to do this, a 286 base pair (bp) region was amplified using

```
F515 (Forward):
                                      (SEQ ID NO: 1)
GTGCCAGCMGCCGCGGTAA
and R806 (Reverse):
                                      (SEQ ID NO: 2)
GGACTACHVGGGTWTCTAAT primers (17).
```

Data was demultiplexed first using Illumina's adapter information, and then a second round of demultiplexing was performed.

A total of 103 subjects were randomly selected for inclusion in the stool microbiota analysis. The median age was 48.0 years (minimum, maximum: 19, 85 years), most subjects were white (82.5%), and the majority were female (73.8%). A total of 73 of these subjects participated in the double-blind phase of the study: 36 in the placebo group and 37 in the rifaximin group. Placebo and rifaximin subjects were generally similar with respect to demographic characteristics.

Approximately 4.6 billion total (~2.2 billion×2 paired ends) sequences were generated from the selected stool samples. The analysis was based on the approximately 1.9 billion reads that had a matching RDP (Ribosomal Database Project) family call at a 50% threshold from both non-overlapping paired ends. There were 172 separate families identified from subjects randomly selected. To focus on the taxa with potential clinical relevance, a subset of taxa was identified from the 172 that included the bacterial families that were cultured from the same subjects, bacteria that have been identified by sequencing methods as being perturbed in IBS, and bacterial families that appeared to be changed during the course of the phase 3 study (Table 4). This list also included families of bacteria that contained known pathogens.

TABLE 4

Bacteria Families of Interest
Bacterial Families

| | |
|---|---|
| *Enterobacteriaceae* | *Pasteurellaceae* |
| *Bacteroidaceae* | *Bifidobacteriaceae* |

TABLE 4-continued

Bacteria Families of Interest
Bacterial Families

| | |
|---|---|
| *Clostridiaceae*.1 | *Synergistaceae* |
| *Enterococcaceae* | *Streptococcaceae* |
| *Staphylococcaceae* | *Comamonadaceae* |
| *Pseudomonadaceae* | *Peptococcaceae*.1 |
| *Peptostreptococcaceae* | *Phyllobacteriaceae* |
| *Aeromonadaceae* | *Corynebacteriaceae* |
| *Verrucomicrobiaceae* | *Veillonellaceae* |
| *Clostridiales incertae sedis XIII* | *Campylobacteraceae* |
| *Eubacteriaceae* | *Lactobacillaceae* |
| *Bacillaceae* | *Ruminococcaceae* |

Richness, Diversity and Similarity Analyses:

The Shannon Diversity Index was used to determine the diversity (which takes into account not only the number of bacterial families present, but also the relative abundance of those families) of the stool microbiota at each visit. There was no substantial change in the diversity of the stool microbiota with rifaximin treatment in the OL phase of the study.

Additionally, the evenness of the microbiota was assessed at each visit in the OL phase of the study. The evenness of the microbiota was not affected by rifaximin treatment, with only minor changes in the overall evenness of the microbiota at post-baseline visits.

Figure 11:
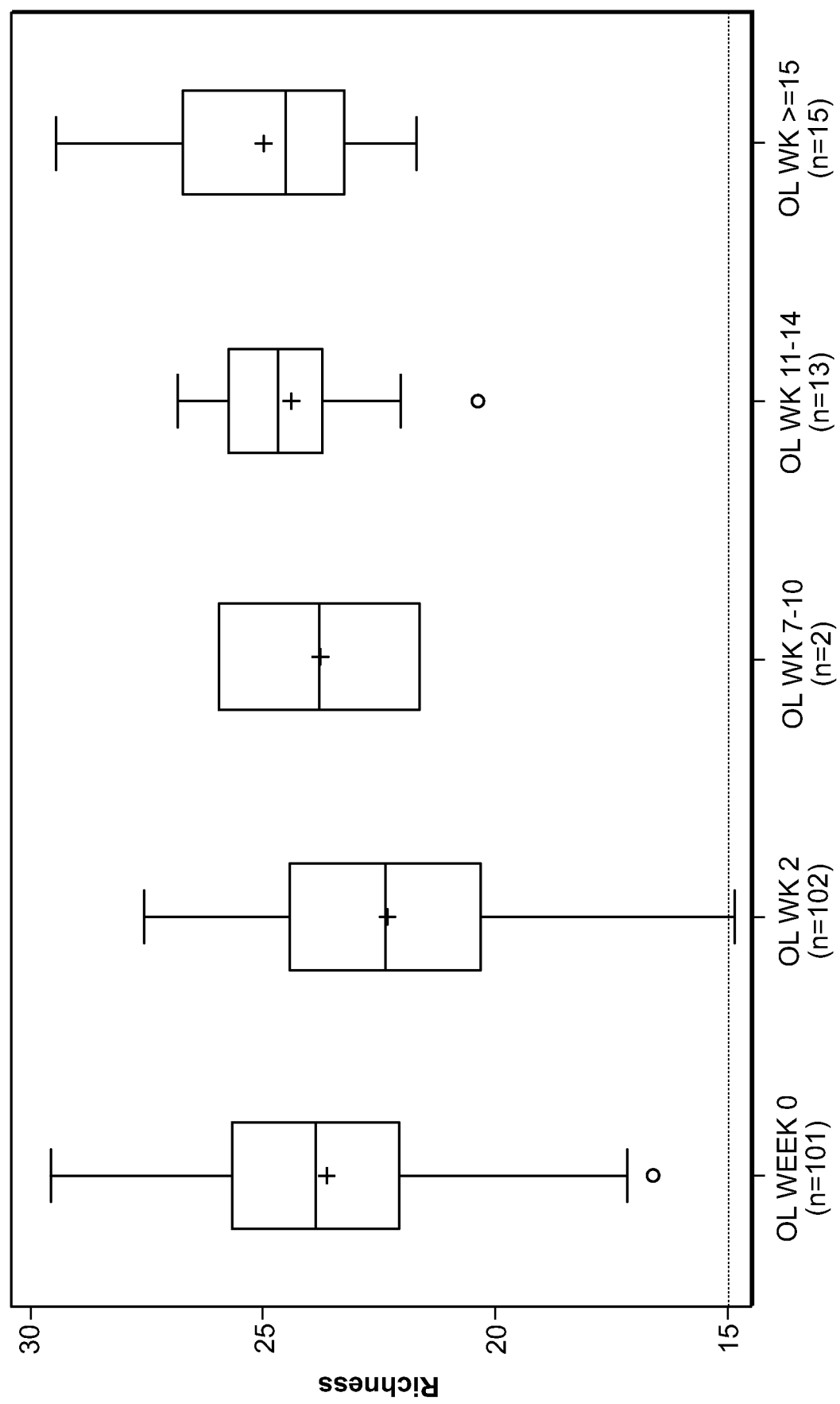
FIG. 11 shows microbiome richness in the open-label phase.
Figure 12:
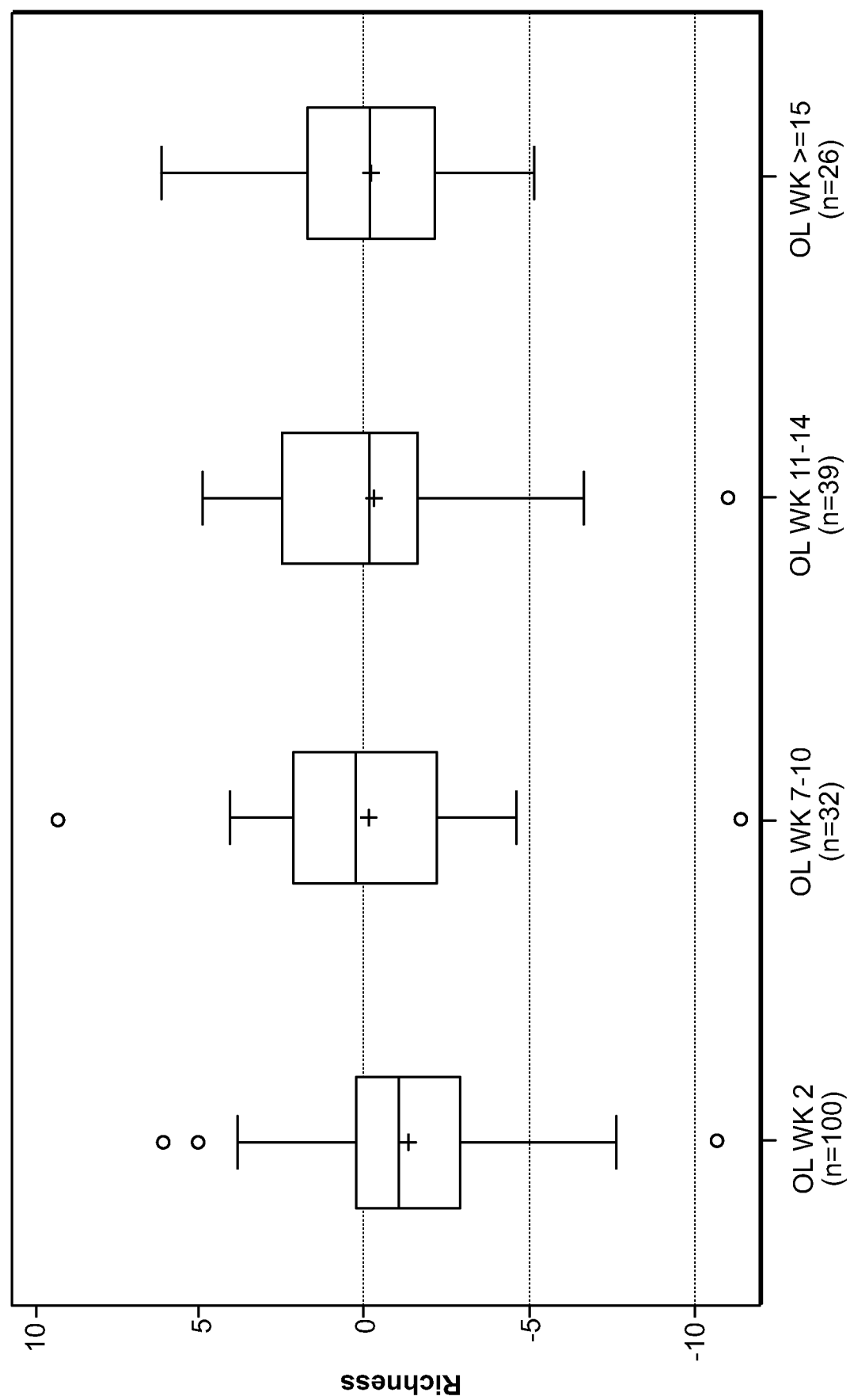
FIG. 12 shows changes from baseline for richness in the open-label phase.

The richness of the microbiota, a measure reflecting the number of bacterial families observed in stool microbiota, appeared to decrease slightly from the pre-treatment baseline to Week 2 in the OL phase, which corresponded to the treatment period for rifaximin (FIG. 11). The richness decreased by 1.235 families from baseline to Week 2. During the follow-up period after the end of the two-week OL rifaximin treatment, richness normalized to baseline levels. FIG. 11 is shown to provide a visual impression of the data, while FIG. 12 shows the change from baseline at Week 2 and during the follow-period of the OL phase.

For bacterial families sequenced from the stool microbiota, the most abundant families sequenced from subjects in the OL phase of the study were the following: Acidaminococcaceae, Bacteroidaceae, Bifidobacteriaceae, Coriobacteriaceae, Enterobacteriaceae, Lachnospiraceae, Prevotellaceae, Rikenellaceae, Ruminococcaceae, Veillonellaceae, and Verrucomicrobiaceae. These eleven (11) families of bacteria represented approximately 90% of the reads on Day 1 of the OL phase of the study. In terms of the bacterial families that were observed to decrease at Week 2 (immediately after two weeks of open-label rifaximin treatment), Bifidobacteriaceae, which represented approximately 2.0% of the population on Day 1, decreased in abundance by between 12% and 49% in comparison to Day 1. Bacteroidaceae, which represented approximately 14% of the overall population on Day 1, increased in abundance by between 1% and 66% at Week 2. It is important to note that some bacterial families, such as Lactobacillaceae, had statistically significant changes from Day 1 to Week 2 in the OL phase of the study, but were of low abundance and therefore would have had a smaller contribution to overall community structure. Likewise, Lactobacillaceae decreased between 8% and 51% at Week 2, but overall, represented 0.2% of the population sequenced. Therefore, it is important not only to consider the changes observed in each family, but also the quantitative contribution they have to the overall stool microbiota.

Richness, Diversity and Similarity Analyses in the Double-Blind Phase:

At baseline of the DB phase of the study, prior to randomization to receive either placebo or rifaximin, the Shannon diversity of the DB placebo and DB rifaximin groups was similar, at 1.733 and 1.786, respectively. After the 2 week treatment period, the Shannon diversity was 1.743 in the placebo group and 1.698 in the DB rifaximin group, with no significant difference between the treatments (p-value=0.4335). The Shannon diversity remained essentially unchanged in the follow-up period, with no statistically significant difference between the treatment groups.

The measure of evenness in the microbiota was also unchanged by either rifaximin or placebo treatment in the DB phase of the study. No significant changes in the evenness of the microbiota were observed within or between the treatment groups.

Figure 13:
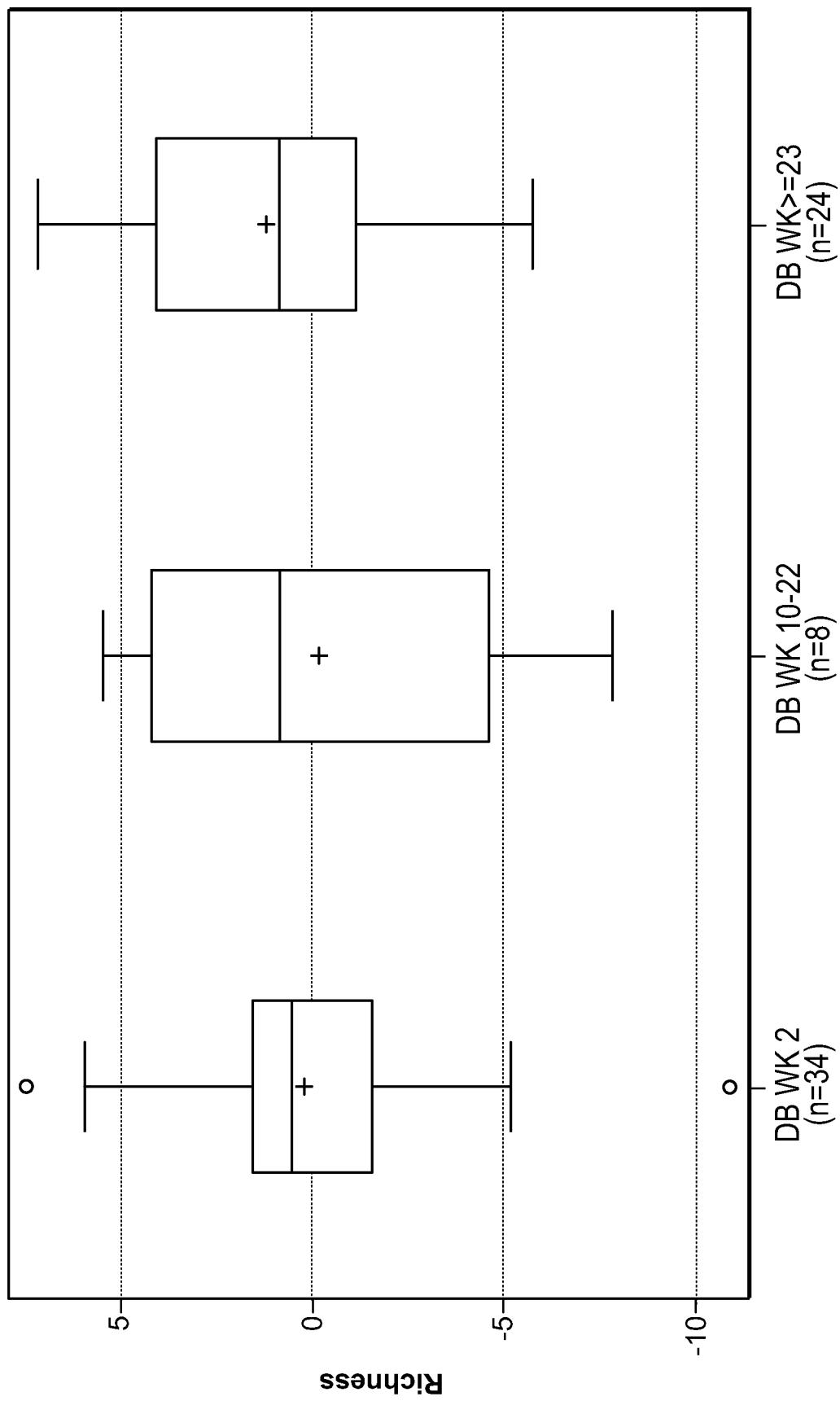
FIG. 13 shows Change from Baseline for Richness in Subjects Receiving Double-Blind.
Figure 14:
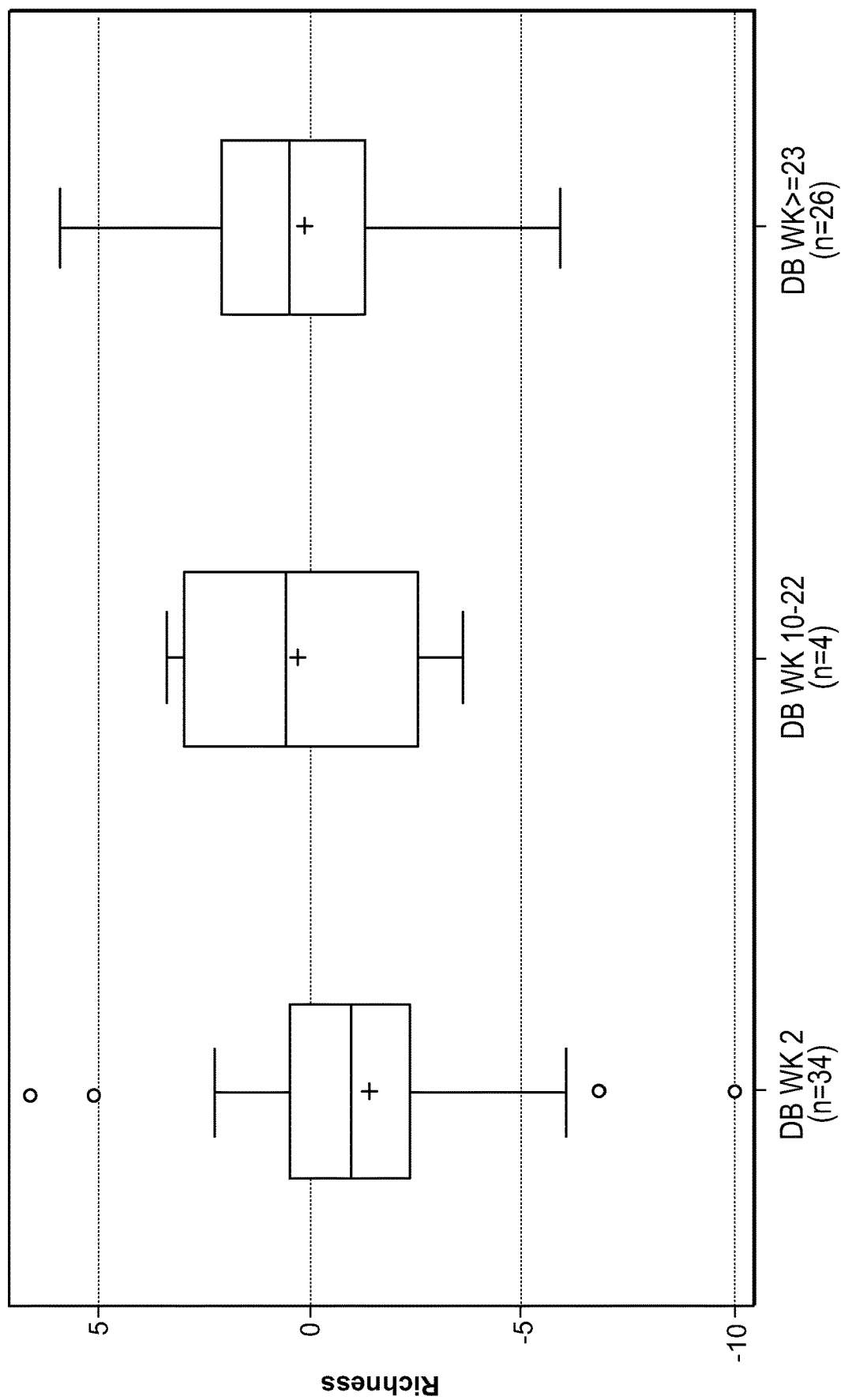
FIG. 14 shows changes from baseline for richness in subjects receiving double-blind rifaximin.

The richness of the microbiota was transiently affected by rifaximin treatment in the DB phase of the study. The richness of the microbiota in subjects treated with DB placebo remained unchanged (FIG. 13), while richness decreased at Week 2 in rifaximin treated subjects (p=0.0331 for a change in the rifaximin treated group from Baseline to Week 2, and p=0.0224 comparing placebo to rifaximin treated subjects at Week 2). In the follow-up period, the decreased richness caused by rifaximin treatment reversed, and there was no significant difference in the richness of the microbiota in placebo or rifaximin treated subjects at any visit in the follow-up period (FIG. 14).

With regards to the bacterial families sequenced from the stool microbiota, the most abundant bacterial families sequenced from subjects in the DB phase of the study were the following: Acidaminococcaceae, Bacteroidaceae, Bifidobacteriaceae, Coriobacteriaceae, Enterobacteriaceae, Lachnospiraceae, Prevotellaceae, Rikenellaceae, Ruminococcaceae, Veillonellaceae, and Verrucomicrobiaceae. These 11 families of bacteria represented approximately 90% of the reads in both the placebo and rifaximin group on Day 1 of the DB phase of the study.

As in the DB phase of the study, there were changes from baseline to the end of treatment at Week 2 in several families of bacteria, but, as in the OL phase, many of these changes occurred in low-abundance families. Changes were evident in both the DB placebo group and the DB rifaximin group. Changes in some families in subjects treated with rifaximin may be related to the antibacterial activity of rifaximin, as was observed with the Clostridiaceae 1 family, which was decreased between 35 and 88% at Week 2 (p-value=0.004). This family represented approximately 0.2% of the sequences in both placebo and rifaximin treated subjects. Rifaximin has been shown to have potent in vitro antibacterial activity against species in the Clostridiaceae family. The abundance of this family returned to baseline the follow-up period. Compared to samples from subjects treated with placebo at Week 2, the decrease observed in Clostridiaceae was not significant (p-value=0.062). Overall, low-abundance taxa showed some effects of rifaximin treatment, but the alterations were transient and recovered by the end of the study.

Figure 15:
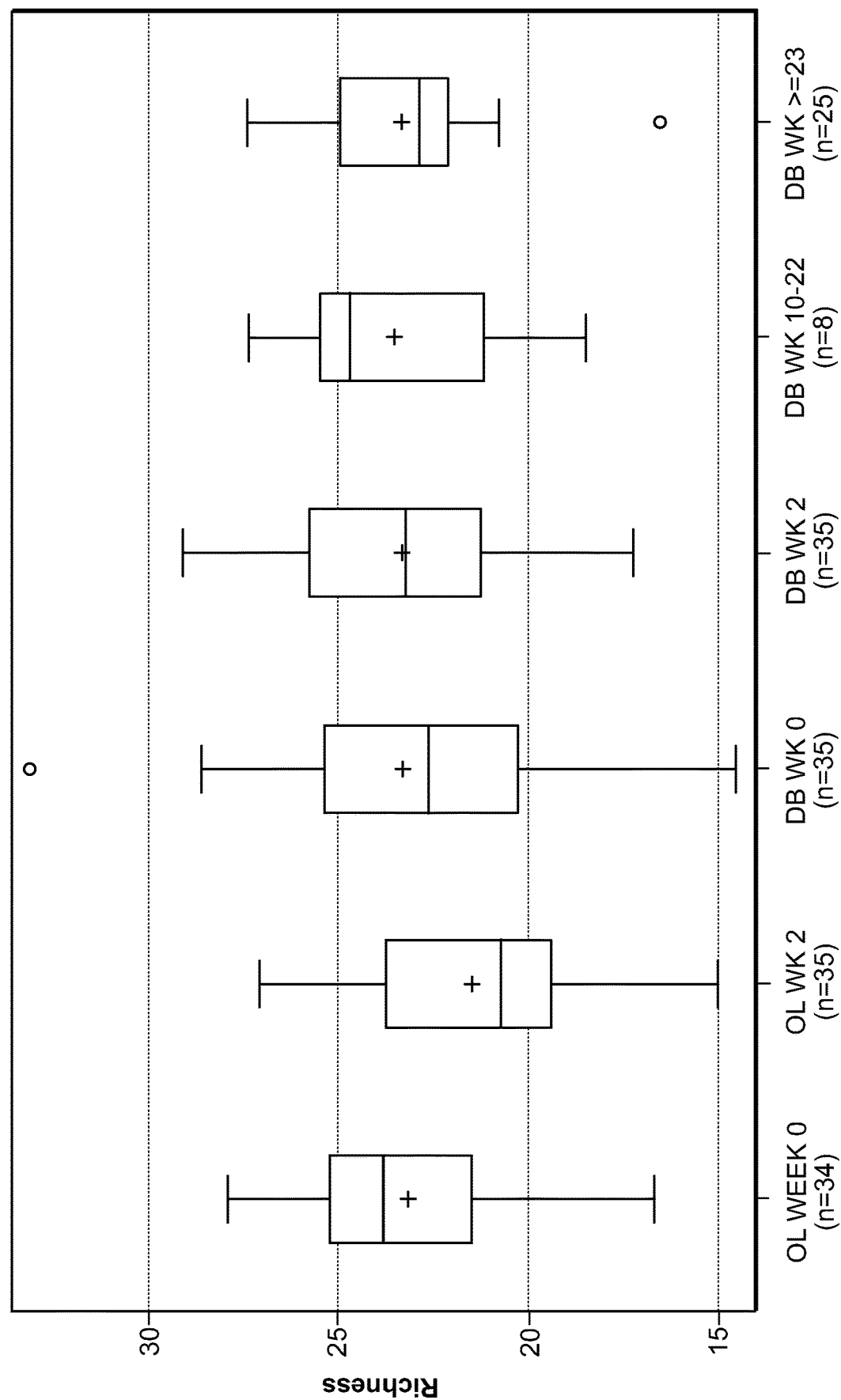
FIG. 15 shows richness of the stool microbiota in double-blind placebo treated subjects in the open-label and double-blind phases.

Analysis of the Microbiota Richness of the Stool Microbiota in Subjects Randomized to Double-Blind Treatment:

The changes in the microbial richness over the course of both the OL and DB phases of RFIB3053 were investigated in the subjects who were randomized to the DB phase of the study to receive either rifaximin (37 subjects) or placebo (36 subjects). The DB placebo treated subjects, who received rifaximin in the OL phase of the study, show a decrease in richness at Week 2 of the OL phase, which recovers by the start of the DB phase (FIG. 15). Additionally, the richness is similar at the start of the OL phase and the end of the DB phase.

Figure 16:
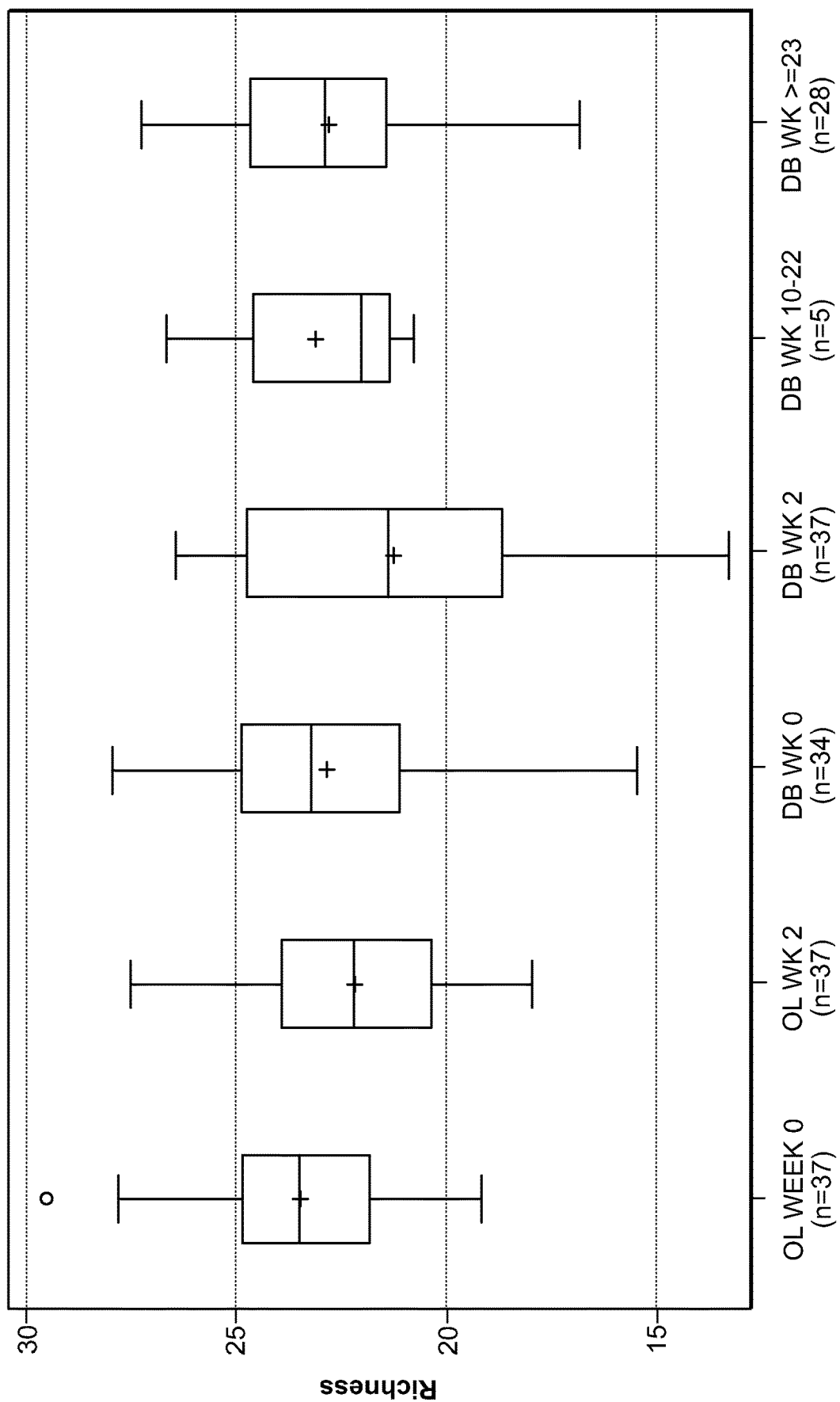
FIG. 16 shows richness of the stool microbiota in double-blind rifaximin treated subjects in the open-label and double-blind phases.

For subjects who received DB rifaximin, decreases in richness are observed at both the OL Week 2 and DB Week 2, corresponding to the end of each rifaximin treatment (FIG. 16). The richness recovered after both treatments, indicating that a long-term suppression of bacterial taxa does not occur following either single or repeat treatment with rifaximin. Rifaximin treatment did not have significant effects on the Shannon diversity or evenness between placebo- and rifaximin-treated subjects with IBS-D, and led to transient changes in the richness of the microbiota. These decreases in richness recovered following the end of the rifaximin treatment course. Of the bacterial families that were affected by rifaximin treatment, sequencing of the 16S rRNA gene revealed that low abundance taxa were more affected by rifaximin treatment than more abundant taxa. Overall, no disturbance of the stool microbiota was observed in subjects during repeat treatment with rifaximin as compared to subjects taking a single course of open-label rifaximin followed by double-blind placebo.

The invention claimed is:

1. A method of diagnosing and treating a subject having IBS, comprising:
   determining that the subject will respond to rifaximin by
      sequencing the V4 hyper-variable region of the 16S rRNA gene of bacteria obtained from a fecal sample of the subject; and
      assigning a number of operational taxonomic units ("OTUs") based on the V4 hyper-variable region of the 16S rRNA gene sequence to one or more taxa selected from Sphingobacteriaceae, Phyllobacteriaceae, Flavobacteriaceae, Sutterellaceae, Thermoanerobacteraceae, and Burkholderialesincertae sedis,
      wherein an OTU includes a cluster of sequences that have at least 97% identity; and
      wherein the subject will respond to rifaximin treatment if the number of OTUs is selected from the group consisting of the OTU of Sphingobacteriaceae greater than 2.056, the OTU of Phyllobacteriaceae greater than 0.540, and the OTU of Flavobacteriaceae greater than 2.928, the OTU of Sutterellaceae less than 3.96, the OTU of Thermoanaerobacteraceae less than 0.253, the OTU of Burkholderialesincertae sedis less than 0.259, and any combination thereof before the rifaximin treatment; and
   administering an effective amount of rifaximin to the subject who will respond to rifaximin treatment.

2. The method of claim 1, wherein the taxon is Sphingobacteriaceae.

3. The method of claim 1, wherein said taxon is Phyllobacteriaceae.

4. The method of claim 1, wherein said taxon is Flavobacteriaceae.

* * * * *

SEQUENCE LISTING

<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gtgccagcmg ccgcggtaa                                              19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic -continued

```
    primer

<400> SEQUENCE: 2
ggactachvg ggtwtctaat                                              20
```